US012778594B2

(12) United States Patent
Lee et al.

(10) Patent No.: US 12,778,594 B2
(45) Date of Patent: Nov. 3, 2026

(54) ADJUSTABLE ARM DEVICE FOR GRASPING TISSUES

(71) Applicant: Evalve, Inc., Santa Clara, CA (US)

(72) Inventors: Benjamin L Lee, Santa Clara, CA (US); Casey Barbarino, San Francisco, CA (US); Chad J Abunassar, Alameda, CA (US)

(73) Assignee: Evalve, Inc., Santa Clara, CA (US)

( * ) Notice: Subject to any disclaimer, the term of this patent is extended or adjusted under 35 U.S.C. 154(b) by 0 days.

(21) Appl. No.: 18/602,184

(22) Filed: Mar. 12, 2024

(65) Prior Publication Data

US 2024/0215985 A1 Jul. 4, 2024

Related U.S. Application Data

(63) Continuation of application No. 17/027,471, filed on Sep. 21, 2020, now Pat. No. 11,957,358, which is a (Continued)

(51) Int. Cl.
*A61B 17/122* (2006.01)
*A61B 17/128* (2006.01)
(Continued)

(52) U.S. Cl.
CPC ........ *A61B 17/1227* (2013.01); *A61B 17/122* (2013.01); *A61B 17/1285* (2013.01);
(Continued)

(58) Field of Classification Search
CPC ...... A61F 2/246; A61F 2/2454; A61F 2/2463; A61F 2/2466; A61B 2017/00243;
(Continued)

(56) References Cited

U.S. PATENT DOCUMENTS 2,097,018 A 10/1937 Chamberlin
2,108,206 A 2/1938 Meeker
(Continued)

FOREIGN PATENT DOCUMENTS

DE 10116168 A1 11/2001
EP 0179562 B1 7/1989
(Continued)

OTHER PUBLICATIONS

Abe et al."De Vega's annuloplasty for acquired tricuspid disease: Early and late results in 110 patients" Ann. Thorac. Surg. (1989) 48:670-676.
(Continued)

*Primary Examiner* — Thomas Mcevoy
(74) *Attorney, Agent, or Firm* — SLEMAN & LUND LLP

(57) ABSTRACT

The present disclosure relates to repair devices configured for use in fixing or approximating tissues, such as cardiac valve tissues and particularly the leaflets of a regurgitant mitral valve. The repair device includes a shaft, a pair of proximal elements pivotally coupled to the shaft and extending from the shaft, and a pair of distal elements pivotally coupled to the shaft and extending from the shaft. The proximal and distal elements are configured so that targeted tissue can be grasped therebetween. The distal elements and/or the proximal elements include adjustable arms that can be extended and retracted to adjust the length of the gripping elements to provide more effective grasping of targeted tissues.

18 Claims, 12 Drawing Sheets

Related U.S. Application Data continuation of application No. 15/373,066, filed on Dec. 8, 2016, now Pat. No. 10,779,837.

(51) Int. Cl.
*A61B 17/29* (2006.01)
*A61B 17/00* (2006.01)
*A61B 90/00* (2016.01)
*A61F 2/24* (2006.01)

(52) U.S. Cl.
CPC .... *A61B 17/29* (2013.01); *A61B 2017/00243* (2013.01); *A61B 2017/00783* (2013.01); *A61B 2017/00845* (2013.01); *A61B 2017/00858* (2013.01); *A61B 2017/00876* (2013.01); *A61B 2017/2926* (2013.01); *A61B 2017/2937* (2013.01); *A61B 2017/2943* (2013.01); *A61B 2017/2944* (2013.01); *A61B 2090/3966* (2016.02); *A61F 2/246* (2013.01); *A61F 2/2466* (2013.01)

(58) Field of Classification Search
CPC ............ A61B 17/29; A61B 2017/2926; A61B 2017/2931; A61B 2017/2943; A61B 2017/2944; A61B 2017/2932; A61B 17/122; A61B 17/1285; A61B 17/1227
See application file for complete search history.

(56) References Cited

U.S. PATENT DOCUMENTS 3,296,668 A 1/1967 Aiken
3,298,688 A 1/1967 Grzybowski
3,378,010 A 4/1968 Codling
3,557,780 A 1/1971 Sato
3,671,979 A 6/1972 Moulopoulos
3,675,639 A 7/1972 Cimber
3,871,979 A 3/1975 Guzman
3,874,338 A 4/1975 Happel
3,874,388 A 4/1975 King
4,007,743 A 2/1977 Blake
4,056,854 A 11/1977 Boretos
4,064,881 A 12/1977 Meredith
4,091,815 A 5/1978 Larsen
4,112,951 A 9/1978 Hulka
4,235,238 A 11/1980 Ogiu
4,297,749 A 11/1981 Davis
4,425,908 A 1/1984 Simon
4,458,682 A 7/1984 Cerwin
4,484,579 A 11/1984 Meno
4,487,205 A 12/1984 Di Giovanni
4,498,476 A 2/1985 Cerwin
4,510,934 A 4/1985 Batra
4,531,522 A 7/1985 Bedi
4,578,061 A 3/1986 Lemelson
4,641,366 A 2/1987 Yokoyama
4,686,965 A 8/1987 Bonnet
4,777,951 A 10/1988 Cribier
4,809,695 A 3/1989 Gwathmey
4,917,089 A 4/1990 Sideris
4,944,295 A 7/1990 Gwathmey
4,969,890 A 11/1990 Sugita
4,994,077 A 2/1991 Dobben
5,015,249 A 5/1991 Nakao
5,019,096 A 5/1991 Fox, Jr.
5,042,707 A 8/1991 Taheri
5,047,041 A 9/1991 Samuels
5,049,153 A 9/1991 Nakao
5,061,277 A 10/1991 Carpentier
5,069,679 A 12/1991 Taheri
5,108,368 A 4/1992 Hammerslag
5,108,388 A 4/1992 Trokel
5,125,758 A 6/1992 Dewan
5,171,252 A 12/1992 Friedland
5,171,259 A 12/1992 Inoue
5,190,554 A 3/1993 Coddington, III
5,195,968 A 3/1993 Lundquist
5,209,756 A 5/1993 Seedhom
5,226,429 A 7/1993 Kuzmak
5,226,911 A 7/1993 Chee
5,234,437 A 8/1993 Sepetka
5,242,456 A 9/1993 Nash
5,250,071 A 10/1993 Palermo
5,251,611 A 10/1993 Zehel
5,254,130 A 10/1993 Poncet
5,261,916 A 11/1993 Engelson
5,271,381 A 12/1993 Ailinger
5,275,578 A 1/1994 Adams
5,282,845 A 2/1994 Bush
5,304,131 A 4/1994 Paskar
5,306,283 A 4/1994 Conners
5,306,286 A 4/1994 Stack
5,312,415 A 5/1994 Palermo
5,314,424 A 5/1994 Nicholas
5,318,040 A 6/1994 Kensey
5,318,525 A 6/1994 West
5,320,632 A 6/1994 Heidmueller
5,325,845 A 7/1994 Adair
5,330,442 A 7/1994 Green
5,332,402 A 7/1994 Teitelbaum
5,342,393 A 8/1994 Stack
5,350,397 A 9/1994 Palermo
5,350,399 A 9/1994 Erlebacher
5,359,994 A 11/1994 Krauter
5,368,564 A 11/1994 Savage
5,368,601 A 11/1994 Sauer
5,383,886 A 1/1995 Kensey
5,391,182 A 2/1995 Chin
5,403,312 A 4/1995 Yates
5,403,326 A 4/1995 Harrison
5,411,552 A 5/1995 Andersen
5,417,699 A 5/1995 Klein
5,417,700 A 5/1995 Egan
5,423,857 A 6/1995 Rosenman
5,423,858 A 6/1995 Bolanos
5,423,882 A 6/1995 Jackman
5,431,666 A 7/1995 Sauer
5,437,551 A 8/1995 Chalifoux
5,437,681 A 8/1995 Meade
5,447,966 A 9/1995 Hermes
5,450,860 A 9/1995 O'Connor
5,456,400 A 10/1995 Shichman
5,456,684 A 10/1995 Schmidt
5,462,527 A 10/1995 Stevens-Wright
5,472,044 A 12/1995 Hall
5,476,470 A 12/1995 Fitzgibbons, Jr.
5,477,856 A 12/1995 Lundquist
5,478,309 A 12/1995 Sweezer
5,478,353 A 12/1995 Yoon
5,478,470 A 12/1995 Fukuda
5,487,746 A 1/1996 Yu
5,496,332 A 3/1996 Sierra
5,498,332 A 3/1996 Handtmann
5,507,725 A 4/1996 Savage
5,507,755 A 4/1996 Gresl
5,507,757 A 4/1996 Sauer
5,520,701 A 5/1996 Lerch
5,522,873 A 6/1996 Jackman
5,527,313 A 6/1996 Scott
5,527,321 A 6/1996 Hinchliffe
5,527,322 A 6/1996 Klein
5,536,251 A 7/1996 Evard
5,540,705 A 7/1996 Meade
5,542,949 A 8/1996 Yoon
5,554,185 A 9/1996 Block
5,562,678 A 10/1996 Booker
5,569,274 A 10/1996 Rapacki
5,571,085 A 11/1996 Accisano, III
5,571,137 A 11/1996 Marlow
5,571,215 A 11/1996 Sterman
5,575,802 A 11/1996 Mcquilkin
5,582,611 A 12/1996 Tsuruta
5,593,424 A 1/1997 Northrup, III

(56) References Cited

U.S. PATENT DOCUMENTS 5,593,435 A 1/1997 Carpentier
5,609,598 A 3/1997 Laufer
5,618,306 A 4/1997 Roth
5,620,452 A 4/1997 Yoon
5,620,461 A 4/1997 Muijs Van De Moer
5,626,588 A 5/1997 Sauer
5,634,932 A 6/1997 Schmidt
5,636,634 A 6/1997 Kordis
5,639,277 A 6/1997 Mariant
5,640,955 A 6/1997 Ockuly
5,649,937 A 7/1997 Bito
5,662,681 A 9/1997 Nash
5,669,917 A 9/1997 Sauer
5,690,671 A 11/1997 McGurk
5,695,504 A 12/1997 Gifford, III
5,695,505 A 12/1997 Yoon
5,702,825 A 12/1997 Keita
5,706,824 A 1/1998 Whittier
5,709,707 A 1/1998 Lock
5,713,910 A 2/1998 Gordon
5,713,911 A 2/1998 Racenet
5,715,817 A 2/1998 Stevens-Wright
5,716,367 A 2/1998 Koike
5,718,725 A 2/1998 Sterman
5,719,725 A 2/1998 Nakao
5,722,421 A 3/1998 Francese
5,725,542 A 3/1998 Yoon
5,725,556 A 3/1998 Moser
5,738,649 A 4/1998 Macoviak
5,741,280 A 4/1998 Fleenor
5,749,828 A 5/1998 Yeung
5,759,193 A 6/1998 Burbank
5,769,812 A 6/1998 Stevens
5,769,863 A 6/1998 Garrison
5,772,578 A 6/1998 Heimberger
5,782,845 A 7/1998 Shewchuk
5,797,927 A 8/1998 Yoon
5,797,960 A 8/1998 Stevens
5,810,847 A 9/1998 Laufer
5,810,849 A 9/1998 Kontos
5,810,853 A 9/1998 Yoon
5,810,876 A 9/1998 Kelleher
5,814,029 A 9/1998 Hassett
5,820,592 A 10/1998 Hammerslag
5,820,631 A 10/1998 Nobles
5,823,955 A 10/1998 Kuck
5,823,956 A 10/1998 Roth
5,824,065 A 10/1998 Gross
5,827,237 A 10/1998 Macoviak
5,829,447 A 11/1998 Stevens
5,833,671 A 11/1998 Macoviak
5,836,955 A 11/1998 Buelna
5,840,081 A 11/1998 Andersen
5,843,031 A 12/1998 Hermann
5,849,019 A 12/1998 Yoon
5,853,422 A 12/1998 Huebsch
5,855,271 A 1/1999 Eubanks
5,855,590 A 1/1999 Malecki
5,855,614 A 1/1999 Stevens
5,860,990 A 1/1999 Nobles
5,861,003 A 1/1999 Latson
5,868,733 A 2/1999 Ockuly
5,876,399 A 3/1999 Chia
5,878,399 A 3/1999 Peralto
5,879,307 A 3/1999 Chio
5,885,258 A 3/1999 Sachdeva
5,885,271 A 3/1999 Hamilton
5,891,160 A 4/1999 Williamson, IV
5,916,147 A 6/1999 Boury
5,928,224 A 7/1999 Laufer
5,944,733 A 8/1999 Engelson
5,947,363 A 9/1999 Bolduc
5,954,732 A 9/1999 Hart
5,957,949 A 9/1999 Leonhardt
5,972,020 A 10/1999 Carpentier
5,972,030 A 10/1999 Garrison
5,980,455 A 11/1999 Daniel
5,989,284 A 11/1999 Laufer
6,007,552 A 12/1999 Fogarty
6,015,417 A 1/2000 Reynolds, Jr.
6,019,722 A 2/2000 Spence
6,022,360 A 2/2000 Reimels
6,033,378 A 3/2000 Lundquist
6,036,699 A 3/2000 Andreas
6,048,351 A 4/2000 Gordon
6,056,769 A 5/2000 Epstein
6,059,757 A 5/2000 Macoviak
6,060,628 A 5/2000 Aoyama
6,060,629 A 5/2000 Pham
6,063,106 A 5/2000 Gibson
6,066,146 A 5/2000 Carroll
6,068,146 A 5/2000 Trent
6,068,628 A 5/2000 Fanton
6,068,629 A 5/2000 Haissaguerre
6,077,214 A 6/2000 Mortier
6,086,600 A 7/2000 Kortenbach
6,088,889 A 7/2000 Luther
6,099,505 A 8/2000 Ryan
6,099,553 A 8/2000 Hart
6,110,145 A 8/2000 Macoviak
6,117,144 A 9/2000 Nobles
6,117,159 A 9/2000 Huebsch
6,123,699 A 9/2000 Webster, Jr.
6,126,658 A 10/2000 Baker
6,132,447 A 10/2000 Dorsey
6,136,010 A 10/2000 Modesitt
6,143,024 A 11/2000 Campbell
6,159,240 A 12/2000 Sparer
6,162,233 A 12/2000 Williamson, IV
6,165,164 A 12/2000 Hill
6,165,183 A 12/2000 Kuehn
6,165,204 A 12/2000 Levinson
6,168,614 B1 1/2001 Andersen
6,171,320 B1 1/2001 Monassevitch
6,182,664 B1 2/2001 Cosgrove
6,187,003 B1 2/2001 Buysse
6,190,408 B1 2/2001 Melvin
6,203,531 B1 3/2001 Ockuly
6,203,553 B1 3/2001 Robertson
6,206,893 B1 3/2001 Klein
6,206,907 B1 3/2001 Marino
6,210,419 B1 4/2001 Mayenberger
6,210,432 B1 4/2001 Solem
6,245,079 B1 6/2001 Nobles
6,267,746 B1 7/2001 Bumbalough
6,267,781 B1 7/2001 Tu
6,269,819 B1 8/2001 Oz
6,277,555 B1 8/2001 Duran
6,283,127 B1 9/2001 Sterman
6,283,962 B1 9/2001 Tu
6,299,637 B1 10/2001 Shaolian
6,306,133 B1 10/2001 Tu
6,312,447 B1 11/2001 Grimes
6,319,250 B1 11/2001 Falwell
6,322,559 B1 11/2001 Daulton
6,332,893 B1 12/2001 Mortier
6,352,708 B1 3/2002 Duran
6,355,030 B1 3/2002 Aldrich
6,358,277 B1 3/2002 Duran
6,368,326 B1 4/2002 Dakin
6,387,104 B1 5/2002 Pugsley, Jr.
6,402,780 B2 6/2002 Williamson, IV
6,402,781 B1 6/2002 Langberg
6,406,420 B1 6/2002 Mccarthy
6,408,420 B1 6/2002 Todoroki
6,419,669 B1 7/2002 Frazier
6,461,366 B1 10/2002 Seguin
6,464,707 B1 10/2002 Bjerken
6,482,224 B1 11/2002 Michler
6,485,489 B2 11/2002 Teirstein
6,508,828 B1 1/2003 Akerfeldt
6,533,796 B1 3/2003 Sauer
6,537,314 B2 3/2003 Langberg
6,540,755 B2 4/2003 Ockuly

(56) References Cited

U.S. PATENT DOCUMENTS

| | | | |
|---|---|---|---|
| 6,551,331 | B2 | 4/2003 | Nobles |
| 6,562,037 | B2 | 5/2003 | Paton |
| 6,562,052 | B2 | 5/2003 | Nobles |
| 6,575,971 | B2 | 6/2003 | Hauck |
| 6,585,761 | B2 | 7/2003 | Taheri |
| 6,599,311 | B1 | 7/2003 | Biggs |
| 6,616,684 | B1 | 9/2003 | Vidlund |
| 6,618,684 | B1 | 9/2003 | Beroset |
| 6,619,291 | B2 | 9/2003 | Hlavka |
| 6,626,899 | B2 | 9/2003 | Houser |
| 6,626,930 | B1 | 9/2003 | Allen |
| 6,628,899 | B1 | 9/2003 | Kito |
| 6,628,930 | B1 | 9/2003 | Vogt |
| 6,629,534 | B1 | 10/2003 | St Goar |
| 6,641,592 | B1 | 11/2003 | Sauer |
| 6,656,221 | B2 | 12/2003 | Taylor |
| 6,669,687 | B1 | 12/2003 | Saadat |
| 6,685,648 | B2 | 2/2004 | Flaherty |
| 6,689,164 | B1 | 2/2004 | Seguin |
| 6,695,866 | B1 | 2/2004 | Kuehn |
| 6,701,929 | B2 | 3/2004 | Hussein |
| 6,702,825 | B2 | 3/2004 | Frazier |
| 6,702,826 | B2 | 3/2004 | Liddicoat |
| 6,709,382 | B1 | 3/2004 | Horner |
| 6,709,456 | B2 | 3/2004 | Langberg |
| 6,718,985 | B2 | 4/2004 | Hlavka |
| 6,719,767 | B1 | 4/2004 | Kimblad |
| 6,723,038 | B1 | 4/2004 | Schroeder |
| 6,726,716 | B2 | 4/2004 | Marquez |
| 6,740,107 | B2 | 5/2004 | Loeb |
| 6,746,471 | B2 | 6/2004 | Mortier |
| 6,752,813 | B2 | 6/2004 | Goldfarb |
| 6,755,777 | B2 | 6/2004 | Schweich, Jr. |
| 6,764,510 | B2 | 7/2004 | Vidlund |
| 6,767,349 | B2 | 7/2004 | Ouchi |
| 6,770,083 | B2 | 8/2004 | Seguin |
| 6,797,001 | B2 | 9/2004 | Mathis |
| 6,797,002 | B2 | 9/2004 | Spence |
| 6,860,179 | B2 | 3/2005 | Hopper |
| 6,875,224 | B2 | 4/2005 | Grimes |
| 6,926,715 | B1 | 8/2005 | Hauck |
| 6,945,978 | B1 | 9/2005 | Hyde |
| 6,949,122 | B2 | 9/2005 | Adams |
| 6,966,914 | B2 | 11/2005 | Abe |
| 6,986,775 | B2 | 1/2006 | Morales |
| 7,004,970 | B2 | 2/2006 | Cauthen, III |
| 7,011,669 | B2 | 3/2006 | Kimblad |
| 7,048,754 | B2 | 5/2006 | Martin |
| 7,112,207 | B2 | 9/2006 | Allen |
| 7,226,467 | B2 | 6/2007 | Lucatero |
| 7,228,467 | B2 | 6/2007 | Ball |
| 7,288,097 | B2 | 10/2007 | Seguin |
| 7,381,210 | B2 | 6/2008 | Zarbatany |
| 7,464,712 | B2 | 12/2008 | Oz |
| 7,497,822 | B1 | 3/2009 | Kugler |
| 7,533,790 | B1 | 5/2009 | Knodel |
| 7,563,267 | B2 | 7/2009 | Goldfarb |
| 7,563,273 | B2 | 7/2009 | Goldfarb |
| 7,604,646 | B2 | 10/2009 | Goldfarb |
| 7,635,329 | B2 | 12/2009 | Goldfarb |
| 7,651,502 | B2 | 1/2010 | Jackson |
| 7,655,015 | B2 | 2/2010 | Goldfarb |
| 7,655,040 | B2 | 2/2010 | Douk |
| 7,666,204 | B2 | 2/2010 | Thornton |
| 8,052,592 | B2 | 11/2011 | Goldfarb |
| 8,348,963 | B2 | 1/2013 | Wilson |
| 8,940,001 | B2 | 1/2015 | Catanese, III |
| 9,572,666 | B2 | 2/2017 | Basude |
| 10,524,912 | B2 | 1/2020 | Wei |
| 10,667,815 | B2 | 6/2020 | Krone |
| 10,779,837 | B2 | 9/2020 | Lee |
| 2001/0004715 | A1 | 6/2001 | Duran |
| 2001/0005787 | A1 | 6/2001 | Oz |
| 2001/0010005 | A1 | 7/2001 | Kammerer |
| 2001/0018611 | A1 | 8/2001 | Solem |
| 2001/0022872 | A1 | 9/2001 | Marui |
| 2001/0037084 | A1 | 11/2001 | Nardeo |
| 2001/0039411 | A1 | 11/2001 | Johansson |
| 2001/0044568 | A1 | 11/2001 | Langberg |
| 2002/0013571 | A1 | 1/2002 | Goldfarb |
| 2002/0022848 | A1 | 2/2002 | Garrison |
| 2002/0026233 | A1 | 2/2002 | Shaknovich |
| 2002/0035361 | A1 | 3/2002 | Houser |
| 2002/0035381 | A1 | 3/2002 | Bardy |
| 2002/0042651 | A1 | 4/2002 | Liddicoat |
| 2002/0055767 | A1 | 5/2002 | Forde |
| 2002/0055774 | A1 | 5/2002 | Liddicoat |
| 2002/0055775 | A1 | 5/2002 | Carpentier |
| 2002/0058910 | A1 | 5/2002 | Hermann |
| 2002/0058995 | A1 | 5/2002 | Stevens |
| 2002/0077687 | A1 | 6/2002 | Ahn |
| 2002/0082621 | A1 | 6/2002 | Schurr |
| 2002/0087148 | A1 | 7/2002 | Brock |
| 2002/0087169 | A1 | 7/2002 | Brock |
| 2002/0087173 | A1 | 7/2002 | Alferness |
| 2002/0103532 | A1 | 8/2002 | Langberg |
| 2002/0107534 | A1 | 8/2002 | Schaefer |
| 2002/0133178 | A1 | 9/2002 | Muramatsu |
| 2002/0147456 | A1 | 10/2002 | Diduch |
| 2002/0156526 | A1 | 10/2002 | Hlavka |
| 2002/0158528 | A1 | 10/2002 | Tsuzaki |
| 2002/0161378 | A1 | 10/2002 | Downing |
| 2002/0169360 | A1 | 11/2002 | Taylor |
| 2002/0183766 | A1 | 12/2002 | Seguin |
| 2002/0183787 | A1 | 12/2002 | Wahr |
| 2002/0183835 | A1 | 12/2002 | Taylor |
| 2003/0005797 | A1 | 1/2003 | Hopper |
| 2003/0045778 | A1 | 3/2003 | Ohline |
| 2003/0050693 | A1 | 3/2003 | Quijano |
| 2003/0069570 | A1 | 4/2003 | Witzel |
| 2003/0069593 | A1 | 4/2003 | Tremulis |
| 2003/0069636 | A1 | 4/2003 | Solem |
| 2003/0074012 | A1 | 4/2003 | Nguyen |
| 2003/0078654 | A1 | 4/2003 | Taylor |
| 2003/0083742 | A1 | 5/2003 | Spence |
| 2003/0105519 | A1 | 6/2003 | Fasol |
| 2003/0105520 | A1 | 6/2003 | Alferness |
| 2003/0120340 | A1 | 6/2003 | Liska |
| 2003/0120341 | A1 | 6/2003 | Shennib |
| 2003/0130669 | A1 | 7/2003 | Damarati |
| 2003/0130730 | A1 | 7/2003 | Cohn |
| 2003/0144697 | A1 | 7/2003 | Mathis |
| 2003/0167071 | A1 | 9/2003 | Martin |
| 2003/0171776 | A1 | 9/2003 | Adams |
| 2003/0187467 | A1 | 10/2003 | Schreck |
| 2003/0195562 | A1 | 10/2003 | Collier |
| 2003/0208231 | A1 | 11/2003 | Williamson |
| 2003/0225423 | A1 | 12/2003 | Huitema |
| 2003/0229395 | A1 | 12/2003 | Cox |
| 2003/0233038 | A1 | 12/2003 | Hassett |
| 2004/0002719 | A1 | 1/2004 | Oz |
| 2004/0003819 | A1 | 1/2004 | St Goar |
| 2004/0019377 | A1 | 1/2004 | Taylor |
| 2004/0019378 | A1 | 1/2004 | Hlavka |
| 2004/0024414 | A1 | 2/2004 | Downing |
| 2004/0030382 | A1 | 2/2004 | St Goar |
| 2004/0039442 | A1 | 2/2004 | St Goar |
| 2004/0039443 | A1 | 2/2004 | Solem |
| 2004/0044350 | A1 | 3/2004 | Martin |
| 2004/0044365 | A1 | 3/2004 | Bachman |
| 2004/0049211 | A1 | 3/2004 | Tremulis |
| 2004/0073302 | A1 | 4/2004 | Rourke |
| 2004/0078053 | A1 | 4/2004 | Berg |
| 2004/0087975 | A1 | 5/2004 | Lucatero |
| 2004/0088047 | A1 | 5/2004 | Spence |
| 2004/0092962 | A1 | 5/2004 | Thornton |
| 2004/0097878 | A1 | 5/2004 | Anderson |
| 2004/0097979 | A1 | 5/2004 | Svanidze |
| 2004/0111099 | A1 | 6/2004 | Nguyen |
| 2004/0122448 | A1 | 6/2004 | Levine |
| 2004/0127981 | A1 | 7/2004 | Rahdert |
| 2004/0127982 | A1 | 7/2004 | Machold |
| 2004/0127983 | A1 | 7/2004 | Mortier |
| 2004/0133062 | A1 | 7/2004 | Pai |

(56) References Cited

U.S. PATENT DOCUMENTS

| | | | |
|---|---|---|---|
| 2004/0133063 | A1 | 7/2004 | Mccarthy |
| 2004/0133082 | A1 | 7/2004 | Abraham-Fuchs |
| 2004/0133192 | A1 | 7/2004 | Houser |
| 2004/0133220 | A1 | 7/2004 | Lashinski |
| 2004/0133240 | A1 | 7/2004 | Adams |
| 2004/0133273 | A1 | 7/2004 | Cox |
| 2004/0138744 | A1 | 7/2004 | Lashinski |
| 2004/0138745 | A1 | 7/2004 | Macoviak |
| 2004/0148021 | A1 | 7/2004 | Cartledge |
| 2004/0152847 | A1 | 8/2004 | Emri |
| 2004/0152947 | A1 | 8/2004 | Schroeder |
| 2004/0153144 | A1 | 8/2004 | Seguin |
| 2004/0158123 | A1 | 8/2004 | Jayaraman |
| 2004/0162610 | A1 | 8/2004 | Liska |
| 2004/0167539 | A1 | 8/2004 | Kuehn |
| 2004/0186486 | A1 | 9/2004 | Roue |
| 2004/0186566 | A1 | 9/2004 | Hindrichs |
| 2004/0193191 | A1 | 9/2004 | Starksen |
| 2004/0215339 | A1 | 10/2004 | Drasler |
| 2004/0220593 | A1 | 11/2004 | Greenhalgh |
| 2004/0220657 | A1 | 11/2004 | Nieminen |
| 2004/0225300 | A1 | 11/2004 | Goldfarb |
| 2004/0236354 | A1 | 11/2004 | Seguin |
| 2004/0243229 | A1 | 12/2004 | Vidlund |
| 2004/0249452 | A1 | 12/2004 | Adams |
| 2004/0249453 | A1 | 12/2004 | Cartledge |
| 2004/0260393 | A1 | 12/2004 | Rahdert |
| 2005/0004583 | A1 | 1/2005 | Oz |
| 2005/0004665 | A1 | 1/2005 | Aklog |
| 2005/0004668 | A1 | 1/2005 | Aklog |
| 2005/0021056 | A1 | 1/2005 | St Goar |
| 2005/0021057 | A1 | 1/2005 | St Goar |
| 2005/0021058 | A1 | 1/2005 | Negro |
| 2005/0033446 | A1 | 2/2005 | Deem |
| 2005/0038508 | A1 | 2/2005 | Gabbay |
| 2005/0049698 | A1 | 3/2005 | Bolling |
| 2005/0055089 | A1 | 3/2005 | Macoviak |
| 2005/0059351 | A1 | 3/2005 | Cauwels |
| 2005/0149014 | A1 | 7/2005 | Hauck |
| 2005/0159810 | A1 | 7/2005 | Filsoufi |
| 2005/0197694 | A1 | 9/2005 | Pai |
| 2005/0197695 | A1 | 9/2005 | Stacchino |
| 2005/0216039 | A1 | 9/2005 | Lederman |
| 2005/0228422 | A1 | 10/2005 | Machold |
| 2005/0228495 | A1 | 10/2005 | Macoviak |
| 2005/0251001 | A1 | 11/2005 | Hassett |
| 2005/0267493 | A1 | 12/2005 | Schreck |
| 2005/0273160 | A1 | 12/2005 | Lashinski |
| 2005/0287493 | A1 | 12/2005 | Novak |
| 2006/0004247 | A1 | 1/2006 | Kute |
| 2006/0015003 | A1 | 1/2006 | Moaddes |
| 2006/0020275 | A1 | 1/2006 | Goldfarb |
| 2006/0030866 | A1 | 2/2006 | Schreck |
| 2006/0030867 | A1 | 2/2006 | Zadno |
| 2006/0030885 | A1 | 2/2006 | Hyde |
| 2006/0058871 | A1 | 3/2006 | Zakay |
| 2006/0064115 | A1 | 3/2006 | Allen |
| 2006/0064116 | A1 | 3/2006 | Allen |
| 2006/0064118 | A1 | 3/2006 | Kimblad |
| 2006/0089671 | A1 | 4/2006 | Goldfarb |
| 2006/0089711 | A1 | 4/2006 | Dolan |
| 2006/0135993 | A1 | 6/2006 | Seguin |
| 2006/0184203 | A1 | 8/2006 | Martin |
| 2006/0190036 | A1 | 8/2006 | Wendel |
| 2006/0195012 | A1 | 8/2006 | Mortier |
| 2006/0229708 | A1 | 10/2006 | Powell |
| 2006/0252984 | A1 | 11/2006 | Rahdert |
| 2006/0293701 | A1 | 12/2006 | Ainsworth |
| 2007/0038293 | A1 | 2/2007 | St Goar |
| 2007/0100356 | A1 | 5/2007 | Lucatero |
| 2007/0118155 | A1 | 5/2007 | Goldfarb |
| 2007/0129737 | A1 | 6/2007 | Goldfarb |
| 2007/0162125 | A1 | 7/2007 | LeBeau |
| 2007/0197858 | A1 | 8/2007 | Goldfarb |
| 2007/0198082 | A1 | 8/2007 | Kapadia |
| 2007/0213747 | A1 | 9/2007 | Monassevitch |
| 2008/0039935 | A1 | 2/2008 | Buch |
| 2008/0051703 | A1 | 2/2008 | Thornton |
| 2008/0051807 | A1 | 2/2008 | St Goar |
| 2008/0097489 | A1 | 4/2008 | Goldfarb |
| 2008/0167714 | A1 | 7/2008 | St Goar |
| 2008/0183194 | A1 | 7/2008 | Goldfarb |
| 2009/0156995 | A1 | 6/2009 | Martin |
| 2009/0163934 | A1 | 6/2009 | Raschdorf, Jr. |
| 2009/0177266 | A1 | 7/2009 | Powell |
| 2009/0182419 | A1 | 7/2009 | Bolling |
| 2009/0198322 | A1 | 8/2009 | Deem |
| 2009/0270858 | A1 | 10/2009 | Hauck |
| 2009/0326567 | A1 | 12/2009 | Goldfarb |
| 2010/0016958 | A1 | 1/2010 | St Goar |
| 2010/0152753 | A1 | 6/2010 | Menn |
| 2012/0296349 | A1 | 11/2012 | Smith |
| 2013/0035759 | A1 | 2/2013 | Gross |
| 2013/0066341 | A1 | 3/2013 | Ketai |
| 2013/0066342 | A1 | 3/2013 | Dell |
| 2013/0073029 | A1 | 3/2013 | Shaw |
| 2013/0253642 | A1 | 9/2013 | Brecker |
| 2013/0261638 | A1 | 10/2013 | Diamant |
| 2013/0310928 | A1 | 11/2013 | John |
| 2014/0066693 | A1 | 3/2014 | Goldfarb |
| 2014/0067054 | A1 | 3/2014 | Chau |
| 2014/0128970 | A1 | 5/2014 | Griffin |
| 2014/0249553 | A1 | 9/2014 | Kimura |
| 2014/0309670 | A1 | 10/2014 | Bakos |
| 2015/0005809 | A1 | 1/2015 | Ayres |
| 2015/0073473 | A1 | 3/2015 | Broom |
| 2015/0257877 | A1 | 9/2015 | Hernandez |
| 2016/0174979 | A1 | 6/2016 | Wei |
| 2016/0287387 | A1 | 10/2016 | Wei |
| 2017/0020521 | A1 | 1/2017 | Krone |
| 2018/0146966 | A1 | 5/2018 | Hernández |
| 2018/0344460 | A1 | 12/2018 | Wei |

FOREIGN PATENT DOCUMENTS

| | | | |
|---|---|---|---|
| EP | 0684012 | A2 | 11/1995 |
| EP | 0727239 | A2 | 8/1996 |
| EP | 0782836 | A1 | 7/1997 |
| EP | 0558031 | B1 | 4/1999 |
| EP | 1199037 | A2 | 4/2002 |
| EP | 1230899 | A1 | 8/2002 |
| EP | 1674040 | A2 | 6/2006 |
| FR | 2768324 | A1 | 3/1999 |
| GB | 1598111 | A | 9/1981 |
| GB | 2151142 | A | 7/1985 |
| JP | 09253030 | A | 9/1997 |
| JP | 11089937 | A | 4/1999 |
| JP | 2000283130 | A | 10/2000 |
| JP | 2015502548 | A | 1/2015 |
| WO | 8100668 | A1 | 3/1981 |
| WO | 1981000668 | | 3/1981 |
| WO | 9101689 | A1 | 2/1991 |
| WO | 1991001689 | | 2/1991 |
| WO | 9118881 | A1 | 12/1991 |
| WO | 1991018881 | | 12/1991 |
| WO | 9212690 | A1 | 8/1992 |
| WO | 1992012690 | | 8/1992 |
| WO | 9418881 | A1 | 9/1994 |
| WO | 94018893 | A1 | 9/1994 |
| WO | 1994018881 | | 9/1994 |
| WO | 1994018893 | | 9/1994 |
| WO | 9511620 | A2 | 5/1995 |
| WO | 1995011620 | | 5/1995 |
| WO | 9515715 | A1 | 6/1995 |
| WO | 1995015715 | | 6/1995 |
| WO | 9614032 | A1 | 5/1996 |
| WO | 1996014032 | | 5/1996 |
| WO | 9620655 | A1 | 7/1996 |
| WO | 1996020655 | | 7/1996 |
| WO | 9622735 | A1 | 8/1996 |
| WO | 1996022735 | | 8/1996 |
| WO | 9630072 | A1 | 10/1996 |
| WO | 1996030072 | | 10/1996 |
| WO | 9718746 | A2 | 5/1997 |

(56) References Cited

FOREIGN PATENT DOCUMENTS

| | | | |
|---|---|---|---|
| WO | 1997018748 | | 5/1997 |
| WO | 9725927 | A1 | 7/1997 |
| WO | 9726034 | A1 | 7/1997 |
| WO | 1997025927 | | 7/1997 |
| WO | 1997026034 | A1 | 7/1997 |
| WO | 9738748 | A2 | 10/1997 |
| WO | 9739688 | A2 | 10/1997 |
| WO | 1997038748 | | 10/1997 |
| WO | 1997039688 | | 10/1997 |
| WO | 9748436 | A2 | 12/1997 |
| WO | 1997048436 | | 12/1997 |
| WO | 9807375 | A1 | 2/1998 |
| WO | 1998007375 | | 2/1998 |
| WO | 9824372 | A1 | 6/1998 |
| WO | 1998024372 | | 6/1998 |
| WO | 9830153 | A1 | 7/1998 |
| WO | 9832382 | A1 | 7/1998 |
| WO | 1998030153 | | 7/1998 |
| WO | 1998032382 | | 7/1998 |
| WO | 9835638 | A1 | 8/1998 |
| WO | 9900059 | A1 | 1/1999 |
| WO | 9901377 | A1 | 1/1999 |
| WO | 1999000059 | | 1/1999 |
| WO | 1999001377 | | 1/1999 |
| WO | 9907354 | A2 | 2/1999 |
| WO | 1999007354 | | 2/1999 |
| WO | 9913777 | A1 | 3/1999 |
| WO | 1999013777 | | 3/1999 |
| WO | 9945853 | A1 | 9/1999 |
| WO | 9966967 | A1 | 12/1999 |
| WO | 1999066967 | | 12/1999 |
| WO | 0002489 | A1 | 1/2000 |
| WO | 0003651 | A1 | 1/2000 |
| WO | 0003759 | A2 | 1/2000 |
| WO | 2000002489 | | 1/2000 |
| WO | 2000003651 | | 1/2000 |
| WO | 2000003759 | | 1/2000 |
| WO | 0012168 | A1 | 3/2000 |
| WO | 2000012168 | | 3/2000 |
| WO | 0044313 | A1 | 8/2000 |
| WO | 2000044313 | | 8/2000 |
| WO | 0059382 | A1 | 10/2000 |
| WO | 0060995 | A2 | 10/2000 |
| WO | 2000059382 | | 10/2000 |
| WO | 2000060995 | | 10/2000 |
| WO | 0100111 | A1 | 1/2001 |
| WO | 0100114 | A1 | 1/2001 |
| WO | 0103651 | A2 | 1/2001 |
| WO | 2001000111 | | 1/2001 |
| WO | 2001000114 | | 1/2001 |
| WO | 2001003651 | | 1/2001 |
| WO | 0126557 | A1 | 4/2001 |
| WO | 0126586 | A1 | 4/2001 |
| WO | 0126587 | A1 | 4/2001 |
| WO | 0126588 | A2 | 4/2001 |
| WO | 0126703 | A1 | 4/2001 |
| WO | 0128432 | A1 | 4/2001 |
| WO | 0128455 | A1 | 4/2001 |
| WO | 2001026557 | | 4/2001 |
| WO | 2001026587 | | 4/2001 |
| WO | 2001026588 | | 4/2001 |
| WO | 2001026703 | | 4/2001 |
| WO | 2001028432 | | 4/2001 |
| WO | 2001028455 | | 4/2001 |
| WO | 0147438 | A1 | 7/2001 |
| WO | 0149213 | A2 | 7/2001 |
| WO | 0150985 | A1 | 7/2001 |
| WO | 2001047438 | | 7/2001 |
| WO | 2001049213 | | 7/2001 |
| WO | 2001050985 | | 7/2001 |
| WO | 0154618 | A1 | 8/2001 |
| WO | 0156512 | A1 | 8/2001 |
| WO | 2001054618 | | 8/2001 |
| WO | 2001056512 | | 8/2001 |
| WO | 0166001 | A2 | 9/2001 |
| WO | 0170320 | A1 | 9/2001 |
| WO | 2001066001 | | 9/2001 |
| WO | 2001070320 | | 9/2001 |
| WO | 0189440 | A2 | 11/2001 |
| WO | 2001089440 | | 11/2001 |
| WO | 0195831 | A2 | 12/2001 |
| WO | 0195832 | A2 | 12/2001 |
| WO | 0197741 | A2 | 12/2001 |
| WO | 2001095831 | | 12/2001 |
| WO | 2001095832 | | 12/2001 |
| WO | 2001097741 | | 12/2001 |
| WO | 0200099 | A2 | 1/2002 |
| WO | 0201999 | A2 | 1/2002 |
| WO | 0203892 | A1 | 1/2002 |
| WO | 2002000099 | | 1/2002 |
| WO | 2002001999 | | 1/2002 |
| WO | 2002003892 | | 1/2002 |
| WO | 2002034167 | A2 | 5/2002 |
| WO | 02060352 | A1 | 8/2002 |
| WO | 02062263 | A2 | 8/2002 |
| WO | 02062270 | A1 | 8/2002 |
| WO | 02062408 | A2 | 8/2002 |
| WO | 2002060352 | | 8/2002 |
| WO | 2002062263 | | 8/2002 |
| WO | 2002062270 | | 8/2002 |
| WO | 2002062408 | | 8/2002 |
| WO | 03001893 | A2 | 1/2003 |
| WO | 03003930 | A1 | 1/2003 |
| WO | 2003001893 | | 1/2003 |
| WO | 03020179 | A1 | 3/2003 |
| WO | 2003020179 | | 3/2003 |
| WO | 03028558 | A2 | 4/2003 |
| WO | 2003028558 | | 4/2003 |
| WO | 03037171 | A2 | 5/2003 |
| WO | 2003037171 | | 5/2003 |
| WO | 03047467 | A1 | 6/2003 |
| WO | 03049619 | A2 | 6/2003 |
| WO | 2003047467 | | 6/2003 |
| WO | 2003049619 | | 6/2003 |
| WO | 03073910 | A2 | 9/2003 |
| WO | 03073913 | A2 | 9/2003 |
| WO | 2003073910 | | 9/2003 |
| WO | 2003073913 | | 9/2003 |
| WO | 03082129 | A2 | 10/2003 |
| WO | 2003082129 | | 10/2003 |
| WO | 03105667 | A2 | 12/2003 |
| WO | 2003105667 | | 12/2003 |
| WO | 2004004607 | A1 | 1/2004 |
| WO | 2004012583 | A2 | 2/2004 |
| WO | 2004012789 | A2 | 2/2004 |
| WO | 2004014282 | A2 | 2/2004 |
| WO | 2004019811 | A2 | 3/2004 |
| WO | 2004030570 | A2 | 4/2004 |
| WO | 2004037317 | A2 | 5/2004 |
| WO | 2004045370 | A2 | 6/2004 |
| WO | 2004045378 | A2 | 6/2004 |
| WO | 2004045463 | A2 | 6/2004 |
| WO | 2004047679 | A1 | 6/2004 |
| WO | 2004062725 | A1 | 7/2004 |
| WO | 2004082523 | A2 | 9/2004 |
| WO | 2004082538 | A2 | 9/2004 |
| WO | 2004093730 | A2 | 11/2004 |
| WO | 2004103162 | A2 | 12/2004 |
| WO | 2004112585 | A2 | 12/2004 |
| WO | 2004112651 | A2 | 12/2004 |
| WO | 2005002424 | A2 | 1/2005 |
| WO | 2005018507 | A2 | 3/2005 |
| WO | 2005027797 | A1 | 3/2005 |
| WO | 2005032421 | A2 | 4/2005 |
| WO | 2005062931 | A2 | 7/2005 |
| WO | 2005112792 | A2 | 12/2005 |
| WO | 2006037073 | A2 | 4/2006 |
| WO | 2006105008 | A1 | 10/2006 |
| WO | 2006105009 | A1 | 10/2006 |
| WO | 2006115875 | A2 | 11/2006 |
| WO | 2006115876 | A2 | 11/2006 |
| WO | 2007009099 | A2 | 1/2007 |
| WO | 2007038608 | A2 | 4/2007 |
| WO | 2011034973 | A2 | 3/2011 |

(56) References Cited

FOREIGN PATENT DOCUMENTS

| | | | |
|---|---|---|---|
| WO | 2014138482 | A1 | 9/2014 |
| WO | 2016161135 | A1 | 10/2016 |
| WO | 2017015288 | A2 | 1/2017 |
| WO | 2018102310 | A1 | 6/2018 |
| WO | 2018106482 | A1 | 6/2018 |

OTHER PUBLICATIONS

Agricola et al., "Mitral valve reserve in double orifice technique: an exercise echocardiographic study," Journal of Heart Valve Disease(2002)11(5):637 643.
Alfieri et al., "An effective technique to correct anterior mitral leaflet prolapse," J Card Surg(1999) 14(6):468-470.
Alfieri et al., "Novel suture device for beating heart mitral leaflet approximation," Annals of Thoracic Surgery(2002) 74:1488 1493.
Alfieri et al., "The double orifice technique in mitral valve repair: a simple solution for complex problems," Journal of Thoracic Cardiovascular Surgery(2001) 122:674 681.
Alfieri et al., "The edge to edge technique," The European Association for Cardio-Thoracic Surgery 14th Annual Meeting, Oct. 7-11, 2000 Book of Proceedings. 3 pages.
Alfieri, "The edge-to-edge repair of the mitral valve," [Abstract] 6th Annual NewEra Cardiac Care: Innovation & Tecnology, Heart Surgery Forum(2003) pp. 103.
Alvarez et al., "Repairing the degenerative mitral valve: Ten- to fifteen-year follow-up" J. Thorac. Cardiovasc. Surg. (1996) 112:238-247.
Arisi et al., "Mitral valve repair with Alfieri technique in mitral regurgitation of diverse etiology: early echocardiographic results," Circulation Supplement II(2001) 104(17):3240.
Bach et al., "Early improvement in congestive heart failure after correction of secondary mitral regurgitation in end-stage cardiomyopathy," Am. Heart J.(1995) 129:1165-1170.
Bach et al., "Improvement following correction of secondary mitral regurgitation in end-stage cardiomyopathy with mitral annuloplasty" Am. J. Cardiol. (1996) 78:966-969.
Bailey, "Surgery of the Heart," Chapter 20(1995) pp. 686-737.
Bernal et al."The 'Valve Racket': a new and different concept of atrioventricular valve repair," Eur. J. Cardio-thoracic Surgery 29:1026-29 (2006).
Bhudia et al., "Edge-to-edge (Alfieri) mitral repair: results in diverse clinical settings," Ann Thorac Surg, 77: 1598-1606 (2004).
Bhudia, #58 Edge-to-edge mitral repair: a versatile mitral repair technique, 2003 STS Presentation[Abstract Only]. 2 pages.
Bolling et al, Surgery for Acquired Heart Disease: Early Outcome of Mitral Valve Reconstruction in Patients with End-stage Cardiomyopathy, J. Thor. and Cariovasc. Surg., Apr. 1995, pp. 676-683, vol. 109.
Borghetti et al., "Preliminary observations on haemodynamics during physiological stress conditions following 'double-orifice' mitral valve repair," European Journal of Cardio-thoracic Surgery, Apr. 18(2001) 20:262-269.
Castedo, "Edge-to-Edge Tricuspid Repair for Redeveloped Valve Incompetence after DeVega's Annuloplasty," Ann Thora Surg., 75:605-606 (2003).
Dec et al., "Idiopathic dilated cardiomyopathy," N. Engl. J. Med. (1994) 331:1564-1575. 12 pages.
Dottori et al., "Echocardiographic imaging of the Alfieri type mitral valve repair," Ital Heart J(2001) 2(4):319-320.
Downing et al., "Beating heart mitral valve surgery: Preliminary model and methodology," Journal of Thoracic and Cardiovascular Surgery(2002) 123(6):1141-1146.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al. "Restoring Optimal Surface of Coaptation With a Mini Leaflet Prosthesis: A New Surgical Concept for the Correction of Mitral Velve Prolapse," Int'l. Soc. for Minimally Invasive Cardiothoracic Surgery 1(4):186-87 (2006).
Frazier et al., #62 Early Clinical Experience With An Implantable, Intracardiac Circulatory Support Device: Operative Considerations And Physiologic Implications, 2003 STS Presentation 1 page total. [Abstract Only].
Fucci et al, Improved Results with Mitral Valve Repair Using New Surgical Techniques, Eur. J. Cardiothorac. Surg., Nov. 1995, pp. 621-627, vol. 9.
Fundaro et al., "Chordal plication and free edge remodeling for mitral anterior leaflet prolapse repair: 8-year follow-up," Annals of Thoracic Surgery(2001) 72:1515-1519.
Garcia-Rinaldi et al., "Left ventricular vol. reduction and reconstruction is ischemic cardiomyopathy," Journal of Cardiac Surgery(1999) 14:199-210.
Gateliene, "Early and postoperative results results of metal and tricuspid valve insufficiency surgical treatment using edge-to-edge central coaptation procedure," Medicina 38 (Suppl 2): 172-175 (2002) [Article in LithuanianEnglish summary on p. 174 of the article].
Gatti et al."The edge to edge technique as a trick to rescue an imperfect mitral valve repair," Eur J Cardiothorac Surg. (2002) 22(5):817 20.
Gillinov et al., "Is Minimally Invasive Heart Valve Surgery a Paradigm for the Future?" Current Cardiology Reports, 1:318-322 (1999).
Gundry et al., "Facile Mitral Valve Repair Utilizing Leaflet Edge Approximation: Midterm Results of the Alfieri Figure of Eight Repair," The Western Thoracic Surgical Association, Scientific Session (May 1999). 1 page.
Gupta et al., #61 Influence Of Older Donor Grafts On Heart Transplant Survival: Lack Of Recipient Effects, 2003 STS Presentation[Abstract Only]. 1 page.
Ikeda et al., "Batista's operation with coronary artery bypass grafting and mitral valve plasty for ischemic dilated cardiomyopathy," The Japanese Journal of Thoracic and Cardiovascular Surgery(2000) 48:746-749.
Izzat et al., "Early experience with partial left ventriculectomy in the Asia-Pacific Region," Annuals of Thoracic Surgery (1999) 67:1703-1707.
Källner et al., "Transaortic approach for the Alfieri Stitch," Ann Thorac Surg(2001) 71:378-380.
Kameda et al, Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade atrial septostomy: Experience with the first 50 procedures" Cathet. Cardiovasc. Diagn(1991) 23:257-262.
Kherani et al., "Edge-to-edge mitral valve repair: the Columbia Presbyterian experience," Ann Thorac Surg2004; 78: 73-76.
Konertz et at, "Results after partial left ventriculectomy in a European heart failure population," Journal of Cardiac Surgery(1999) 14(2):129-135.
Kron et al., "Surgical relocation of the posterior papillary muscle in chronic ischemic mitral regurgitation," Annals. of Thoracic Surgery(2002)74:600 601.
Krüger et al, "Edge to edge technique in complex mitral valve repair," Thorac Cardiovasc Surg, (2000) Thema: Posterhttp://www.thieme.de/thoracic/abstracts/abstracts/p-73.html.
Langer et al."Posterior mitral leaflet extensions: An adjunctive repair option for ischemic mitral regurgitation?," J. Thorac. Cardiovasc. Surf. 131:868-77 (2006).
Lorusso et al., "Double-Orifice" technique to repair extensive mitral valve excision following acute endocarditis, J Card Surg(1998) 13:24-26.
Lorusso et al., "The double-orifice technique for mitral valve construction: predictors of postoperative outcome," Eur J. Cardiothorac Surg(2001) 20(3):583-589.
Maisano et al., "The double orifice repair for Barlow Disease: a simple solution for a complex repair," Supplement I Circulation(1999) 100(18):1-94.

(56) References Cited

OTHER PUBLICATIONS

Maisano et al., "The double orifice technique as a standardized approach to treat mitral regurgitation due to severe myxomatous disease: surgical technique," European Journal of Cardiothoracic Surgery(2000) 17:201-215.
Maisano et al., "The edge-to-edge technique: A simplified method to correct mitral insufficiency" Eur. J. Cardiothorac. Surg.(1998) 13:240-246.
Maisano et al., "The hemodynamic effects of double-orifice valve repair for mitral regurgitation: a 3D computational model," European Journal of Cardio-thoracic Surgery(1999) 15:419-425.
Maisano et al., "Valve repair for traumatic tricuspid regurgitation," Eur J. Cardio-thorac Surg(1996) 10:867-873.
Mantovani et al., "Edge-to-edge repair of congenital familiar tricuspid regurgitation: case report," J. Heart Valve Dis. (2000) 9 (5):641-643.
McCarthy and Cosgrove et al."Tricuspid Valve Reapir with the Cosgrove-Edwards Annuloplasty System," Ann. Thorac. Surg. 64:267-268 (1997).
Mccarthy et al., "Partial left ventriculectomy and mitral valve repair for end-stage congestive heart failure," European Journal of Cardio-thoracic Surgery(1998) 13:337-343.
Moainie et al., Correction of traumatic tricuspid regurgitation using the double orifice technique, Annals of Thoracic Surgery(2002) 73:963 965.
Morales et al., "Development of an off bypass mitral valve repair," The Heart Surgery Forum #1999-4963(1999) 2 (2):115-120.
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):1-Jan. 29, 35 (2001).
Noera et al . . . , "Tricuspid Valve Incompetence Caused by Nonpenetrating Thoracic Trauma", Annals of Thoracic Surgery, 1991, 51 (2)320-322.
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al."Clinical use of a blade atrial septostomy" Circulation (1978) 58:600-608.
Patel et al., #57 Epicardial Atrial Defibrillation: Novel Treatment Of Postoperative Atrial Fibrillation, 2003 STS Presentation[Abstract Only]. 1 page.
Privitera et al."Mitral Valve Repair: Clinical Outcome and Pathology; Circulation," (2002) 106:173.
Redaelli et al., "A Computational Study of the Hemodynamics After 'Edge-To-Edge' Mitral Valve Repair," Journal of Biomechanical Engineering, 123:565-570 (2001).
Reul, "Mital valve reconstruction for mitral insufficiency," Progress in Cardiovascular Diseases, (1997) vol. XXXIX, No. 6pp. 567-599.
Ricchi et al., Linear Segmental Annuloplasty for Mitral Valve Repair, Ann. Thorac. Surg., Jan. 7, 1997, pp. 1805-1806, vol. 63.
Robicsek et al., #60 The Bicuspid Aortic Valve: How Does It Function? Why Does It Fail?, 2003 STS Presentation [Abstract Only]. 1 page.
Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Tamura et al., "Edge to Edge Repair for Mitral Regurgitation in a Patient with Chronic Hemodialysis: Report of A Case," Kyobu Geka. The Japanese Journal of Thoracic Surgery, 54(9):788-790 (2001).
Tibayan et al., #59 Annular Geometric Remodeling In Chronic Ischemic Mitral Regurgitation, 2003 STS Presentation [Abstract Only]. 2 pages.
Timek, "Edge-to-edge mitral repair: gradients and three-dimensional annular dynamics in vivo during inotropic stimulation," European Journal of Cardio-thoracic Surgery, (2001)19:431-437.
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery(1999) 15:119-126.
Uchida et al., "Percutaneous cardiomyotomy and valvultomy with angioscopic guidance," Am. Heart J.(1991) 121:1221-1224.
Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
Umana et al., "'Bow-tie' Mitral Valve Repair Successfully Addresses Subvalvular Dysfunction in Ischemic Mitral Regurgitation," Surgical Forum, XLVIII:279-280 (1997).
Votta et al., "3 D computational analysis of the stress distribution on the leaflets after edge to edge repair of mitral regurgitation," Journal of Heart Valve Disease(2002)11:810 822.

ADJUSTABLE ARM DEVICE FOR GRASPING TISSUES

CROSS-REFERENCE TO RELATED APPLICATIONS

This application is a continuation of U.S. patent application Ser. No. 17/027,471, filed Sep. 21, 2020, which is a continuation of U.S. patent application Ser. No. 15/373,066, filed Dec. 8, 2016, which is now U.S. Pat. No. 10,779,837, the contents of which are incorporated herein by reference in their entireties.

BACKGROUND

The mitral valve controls blood flow from the left atrium to the left ventricle of the heart, preventing blood from flowing backwards from the left ventricle into the left atrium so that it is instead forced through the aortic valve for delivery of oxygenated blood throughout the body. A properly functioning mitral valve opens and closes to enable blood flow in one direction. However, in some circumstances the mitral valve is unable to close properly, allowing blood to regurgitate back into the atrium. Such regurgitation can result in shortness of breath, fatigue, heart arrhythmias, and even heart failure.

Mitral valve regurgitation has several causes. Functional mitral valve regurgitation (FMR) is characterized by structurally normal mitral valve leaflets that are nevertheless unable to properly coapt with one another to close properly due to other structural deformations of surrounding heart structures. Other causes of mitral valve regurgitation are related to defects of the mitral valve leaflets, mitral valve annulus, or other mitral valve tissues. In some circumstances, mitral valve regurgitation is a result of infective endocarditis, blunt chest trauma, rheumatic fever, Marfan syndrome, carcinoid syndrome, or congenital defects to the structure of the heart. Other cardiac valves, in particular the tricuspid valve, can similarly fail to properly close, resulting in undesirable regurgitation.

Heart valve regurgitation is often treated by replacing the faulty valve with a replacement valve implant or by repairing the valve through an interventional procedure. However, issues can arise related to deployment and effectiveness of various treatment options. For instance, properly positioning and aligning a repair device with respect to a targeted valve can be difficult, particularly considering that the valve leaflets and other structures are continuously moving within the dynamic cardiac environment. Further, grasping and properly gripping tissues of a targeted valve can be difficult. In particular, in a transcatheter procedure with numerous size constraints, the limited size of an interventional device delivered to the targeted site often provides insufficient structure for grasping and gripping the targeted tissue.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein are directed to repair devices configured for use in fixing or approximating tissues in an interventional procedure, including approximating cardiac valve tissues such as the leaflets of a regurgitant cardiac valve, and in particular, a regurgitant mitral valve. In some embodiments, a repair device includes a shaft, a first distal gripping element extending from the shaft, and a first proximal gripping element extending from the shaft. The first distal gripping element and the first proximal gripping element each have medial ends which are pivotally connected to the shaft, and lateral ends which extend away from and are unconnected to the shaft so that the respective gripping elements can be pivoted about the shaft. The first proximal gripping element is configured to cooperate with the distal gripping element to grasp targeted tissue therebetween. At least one adjustable arm is also included. The adjustable arm is coupled to an associated distal gripping element or proximal gripping element so that, upon actuation, the adjustable arm extends to lengthen a lateral reach of the associated gripping element.

In some embodiments, the adjustable arm extends by translating laterally relative to the associated gripping element, and likewise retracts by translating medially relative to the associated gripping element. In some embodiments, the associated gripping element is configured as a track at least partially encompassing the adjustable arm to allow translation of the adjustable arm while maintaining mechanical association with the adjustable arm.

In some embodiments, the adjustable arm extends by rotating about a hinge disposed at a lateral section of the associated gripping element. In some embodiments, the hinge is a torsion spring or other component configured to bias the adjustable arm toward the extended position. In some embodiments, the adjustable arm is associated with the distal gripping element, and is configured to rotate about an inferior side of the distal gripping element when moving between open and retracted positions. In some embodiments, the adjustable arm is associated with the proximal gripping element, and is configured to rotate about a superior side of the proximal gripping element when moving between open and retracted positions.

In some embodiments, the adjustable arm is biased toward an extended position. In some embodiments, a control line is attached to the adjustable arm and is routed medially toward the shaft and then proximally (e.g., through a delivery catheter and to a proximal handle or other control) so that as tension is applied to the control line, the control line moves medially to correspondingly move the adjustable arm toward a retracted position. Likewise, releasing tension allows the biasing force to move the adjustable arm toward the extended position.

In some embodiments, one or more gripping elements are associated with adjustable arms. For example, for a repair device having two proximal gripping elements and two corresponding distal gripping elements, one, two, three, or all four of the gripping elements may be include an adjustable arm. In some embodiments, two distal gripping elements each include an adjustable arm. In some embodiments, two proximal gripping elements each include an adjustable arm. In some embodiments, two distal gripping elements each include an adjustable arm and two proximal gripping elements each include an adjustable arm.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1A:
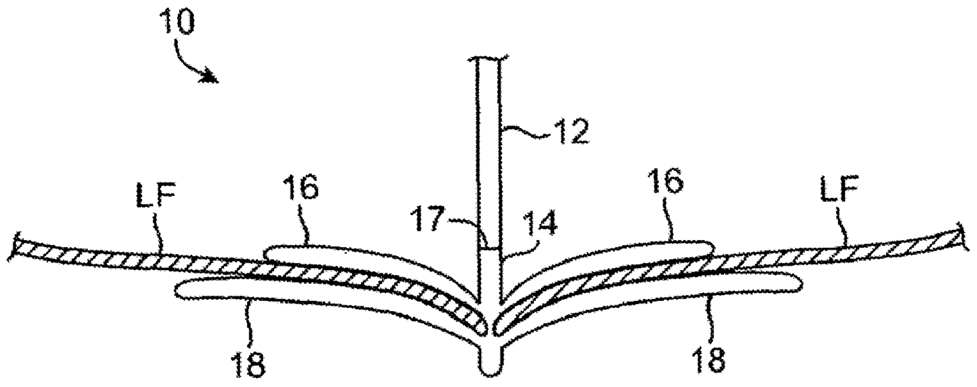
FIGS. 1A-1C illustrate grasping of targeted valve leaflets using a repair device positionable in various positions.

At least some of the embodiments described herein are directed to devices, systems, and methods for stabilizing and grasping tissues such as cardiac valve leaflets, such as mitral valve leaflets, in order to reduce regurgitant flow across the valve. In some embodiments, a repair device is configured as a clip which may be attached to cardiac valve leaflets to approximate the leaflets so that the leaflets can better function to reduce regurgitant flow through the valve. One or more embodiments described herein are directed to clip embodiments having features and components for providing adjustable length arms.

In at least some circumstances, adjustable length arms beneficially provide an extended configuration having increased grasping surface area for improved grasping of tissues, and a retracted configuration providing a smaller profile and smaller length for easier delivery of the repair device to a targeted treatment site. In at least some implementations, the adjustable length arms provide a greater number of interventional options and/or the ability to customize a deployment and grasping procedure according to unique anatomical requirements. For example, one or more arms of a clip device may be adjusted to a desired length or configuration according to intra-procedural needs and/or judgments of an operator in order to enable better tissue grasping and shorter procedure times. In addition, increased lengths to distal and/or proximal elements provided by adjustable length arms can provide a stronger hold and greater engagement to captured tissue, reducing the risk of disengagement or insufficient hold.

In addition, there are occasions where, for a given patient anatomy, overly long arms can grasp too much tissue and bring too much tissue into coaptation, resulting in high diastolic pressure gradients and potential for inducing stenosis. It is therefore beneficial to have an adjustable arm that can be retracted when needed so as to provide more appropriate gradients across the treated valve (typically below about 5 mm Hg). In contrast, there are other circumstances where additional arm length and greater tissue grasping can be beneficial. However, simply lengthening clip arms to a desired length can introduce disadvantages of poor device profile and associated delivery difficulties, and could potentially increase the risk of unwanted interactions between the device and subvalvular structures due to the increased device footprint. One or more of the embodiments described herein overcome these limitations by providing a smaller device profile for delivery which is moveable to an expanded configuration for a final deployed shape.

At least some of the embodiments described herein also enable subsequent "touch up" procedures that beneficially make use of the adjustable functionality of the clip device. For example, following an initial repair procedure where a clip device is implanted, a patient may experience unanticipated residual regurgitation or overly high pressure gradients at later time points. This can occur for a variety of reasons as the treated valve begins to function under the newly imposed structural changes and as the patient recovers from the procedure. An adjustable arm repair device as described herein can beneficially be adjusted in a follow up procedure to correct or better tune the device to the particular patient needs. For example, one or more clip arms may be elongated to enable further regurgitation reduction, or one or more clip arms may be retracted to reduce a diastolic pressure gradient across the treated valve that is deemed to be too dangerous (e.g., for risking stenosis). Tissue overgrowth and bridging of an implanted clip device can typically occur by about 60 days post implantation. This timeframe is a typical limit for touching up or adjusting the implanted clip device post implantation.

Although many of the embodiments described herein are directed to deployment of a repair device at a mitral valve in order to treat a regurgitant mitral valve, it will be understood that the principles, features, and components described herein may also be applied to the treatment, fixation, and/or approximation of other tissues, particularly other cardiac valve tissues (e.g., tricuspid, pulmonary, aortic valves).

FIG. 1A illustrates an interventional device 10 having a delivery device, such as a shaft 12, and a repair device 14. The interventional device 10 is illustrated as having approached a mitral valve from the atrial side and grasped the leaflets (shown as "LF"). The mitral valve may be accessed either surgically or through a transcatheter approach, such as though a transfemoral, transjugular, or transapical approach. In the illustrated embodiment, an antegrade approach, with the device extending from the atrium through the valve, is shown. In other implementations, a retrograde approach may be utilized.

The repair device 14 is releasably attached to the shaft 12 of the interventional device 10 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

The illustrated repair device 14 includes proximal elements 16 and distal elements 18 (each generally referred to herein as "gripping elements"), which protrude radially outward and are positionable on opposite sides of the leaflets so as to capture or retain the leaflets therebetween. The proximal elements 16 are preferably comprised of cobalt chromium, nitinol, or stainless steel, and the distal elements 18 are preferably comprised of a cobalt chromium alloy (such as Elgiloy®) or stainless steel; however any suitable materials may be used. The repair device 14 is attachable to the shaft 12 by a coupling mechanism 17. The coupling mechanism 17 allows the repair device 14 to detach and be left behind as an implant to hold the leaflets together in the coapted position. The coupling mechanism 17 may be a mechanical linkage (e.g., including one or more of a threaded linkage, clasp, clip, pin, tab, receiver slot, or other mechanical fastening component), magnetic linkage, or other coupling means.

In some circumstances, it may be desired to reposition or remove the repair device 14 after the proximal elements 16, distal elements 18, or both have been deployed. Such repositioning or removal may be desired for a variety of reasons, such as to re-approach the valve in an attempt to achieve better valve function, more optimal positioning of the device 14 on the leaflets, better purchase on the leaflets, to detangle the device 14 from surrounding tissue such as chordae, to exchange the device 14 with one having a different design, or to abort the fixation procedure, for example. To facilitate repositioning or removal of the repair device 14 the distal elements 18 are releasable and optionally invertible to a configuration suitable for withdrawal of the device 14 from the valve without tangling or interfering with or damaging the chordae, leaflets, or other tissue.

Figure 1B:
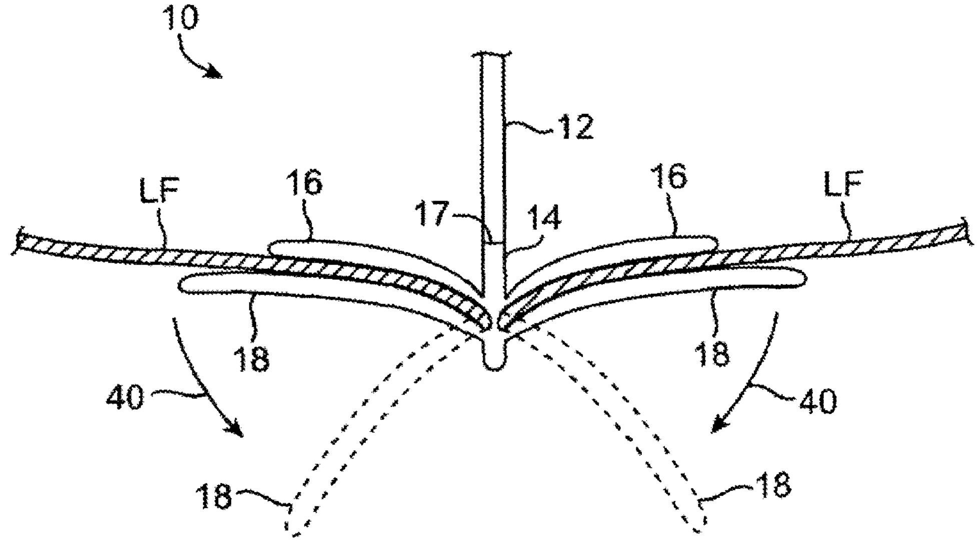
Figure 1C:
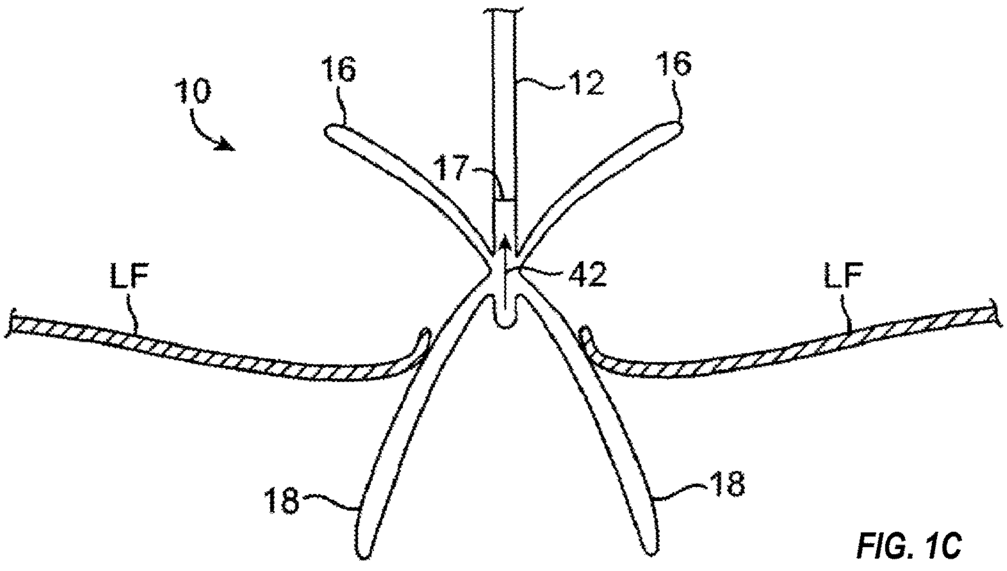

FIG. 1B illustrates an inversion configuration wherein the distal elements 18 are moveable in the direction of arrows 40 to an inverted position. Likewise, the proximal elements 16 may be selectively raised. In the inverted configuration, the repair device 14 may be repositioned to a desired orientation and then the distal elements may be reverted to a deployed/grasping position against the leaflets as shown in FIG. 1A. Alternatively, the repair device 14 may be withdrawn from the leaflets as shown by the arrow 42 in FIG. 1C.

The inverted configuration reduces trauma to the leaflets and minimizes any entanglement of the device with surrounding tissues. Once the device 14 has been withdrawn through the valve leaflets, the proximal and distal elements may be moved to a closed configuration suitable for removal from the body or for reinsertion through the mitral valve.

Figure 2A:
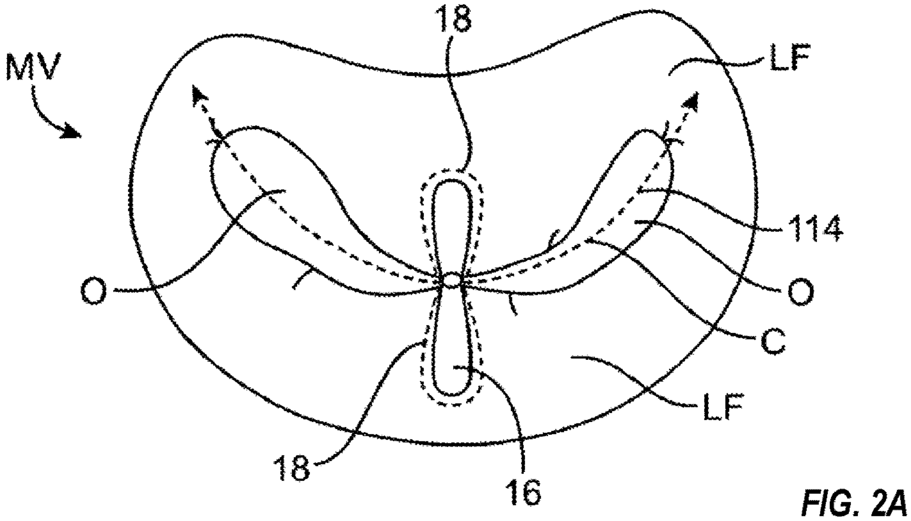
FIGS. 2A-2E illustrate example positions of repair devices in various orientations relative to the targeted valve leaflets.
Figure 2B:
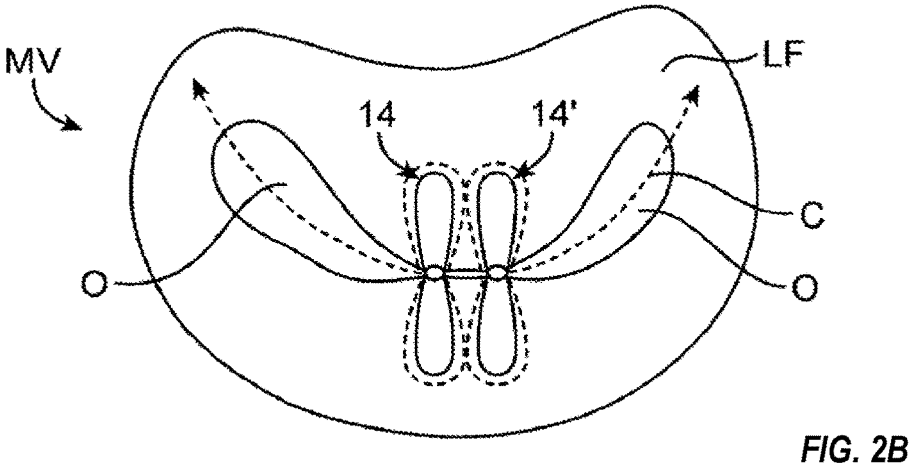
Figure 2C:
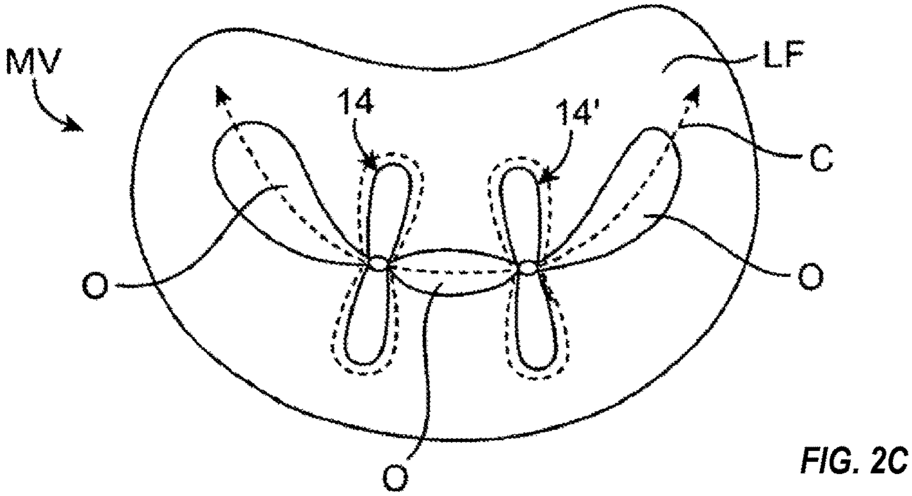

FIGS. 2A-2C illustrate example positions of one or more repair devices 14 in desired orientations in relation to the leaflets of a mitral valve. These are superior views of the mitral valve MV from the atrial side, therefore, the proximal elements 16 are shown in solid line and the distal elements 18 are shown in dashed line. The proximal and distal elements 16 and 18 are typically positioned to be substantially perpendicular to the line of coaptation "C" along coaptation axis 114. The devices 14 may be moved roughly along the line of coaptation to any desired location for fixation. The leaflets are held in place so that during diastole, the leaflets remain in position between the elements 16 and 18 surrounded by openings "O" which result from the diastolic pressure gradient. Upon deployment of one or more repair devices, the captured leaflets may be coapted such that their proximal or upstream surfaces are facing each other in a vertical orientation, parallel to the direction of blood flow through mitral valve. The upstream surfaces may be brought together so as to be in contact with one another or may be held slightly apart, but will preferably be maintained in the vertical orientation in which the upstream surfaces face each other at the point of coaptation.

Referring to FIG. 2A, the placement of one repair device near the center of the leaflets simulates the double orifice geometry of a standard surgical bow-tie repair. Color Doppler echo or other imaging technique may be used to determine if the regurgitation of the valve has been sufficiently reduced. If the resulting mitral flow pattern is satisfactory, the leaflets may be fixed together in this orientation. If the results show insufficient improvement in mitral regurgitation, the repair device 14 may be repositioned. This may be repeated until an optimal or sufficient result is produced. Once the leaflets are coapted in a desired arrangement, the repair device 14 is then detached from the shaft 12 and left behind as an implant to hold the leaflets together in the coapted position.

Figure 2D:
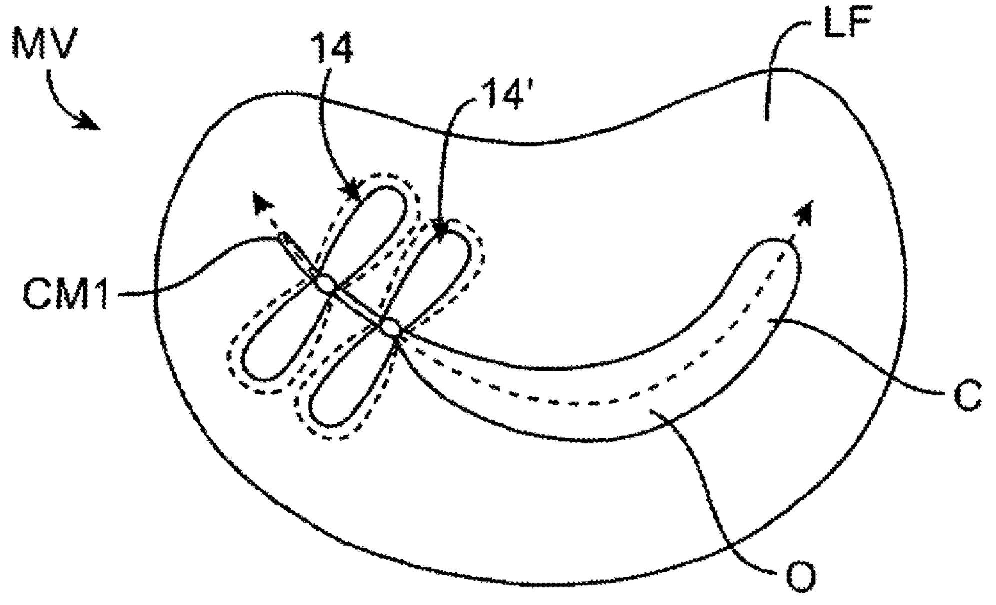

In some circumstances, it may be desired to add an additional fixation element 14', such as illustrated in FIGS. 2B-2E. In FIG. 2B, the additional fixation element 14' is positioned beside a previously placed fixation element 14, retaining the double orifice geometry. In FIG. 2C, the additional fixation element 14' is positioned a distance, such as up to 1 cm, from the previously placed fixation element 14 creating a triple orifice geometry. In FIG. 2D, the fixation elements 14 and 14' are positioned adjacent to each other near a first commissure CM1. Such arrangement creates generally a single orifice geometry by plicating on one side of the valve opening.

Figure 2E:
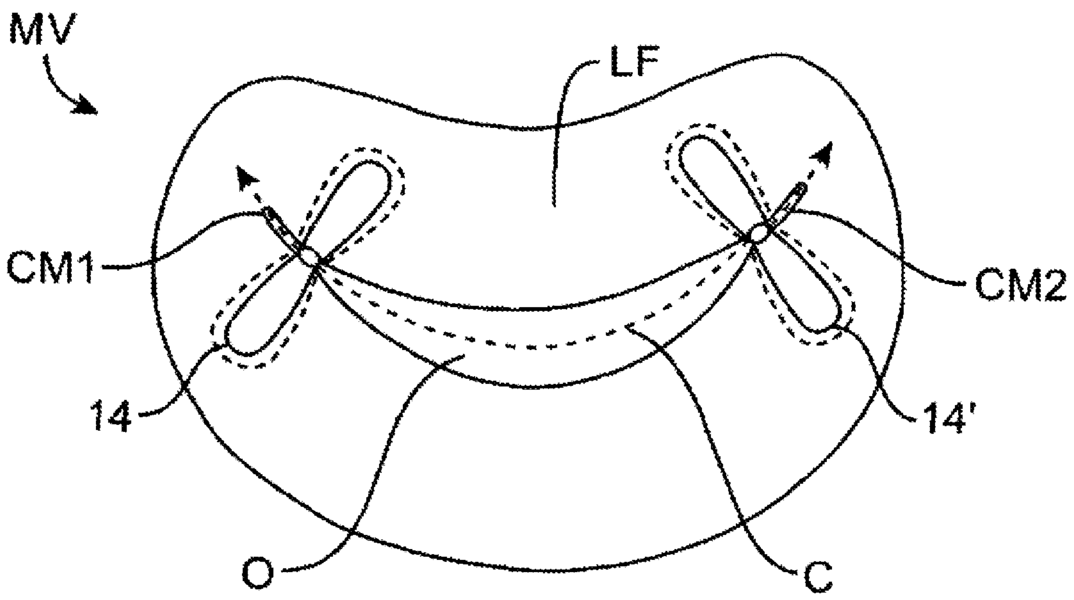

Further, as shown in FIG. 2E, one fixation element 14 may be positioned near the first commissure CM1 and an additional fixation element 14' may be positioned near a second commissure CM2. Such arrangement also creates a single orifice geometry by plicating on either side of the valve opening. The additional fixation element 14' may be desired to ensure adequate fixation of the leaflets LF and/or to further reposition the leaflets LF. The additional fixation element 14' may be added at any time during the procedure or at a separate procedure at a later point in time. It will be understood that any number of fixation elements may be positioned to fixate the leaflets or any other tissue, including two, three, four, five or more fixation elements.

Figure 3:
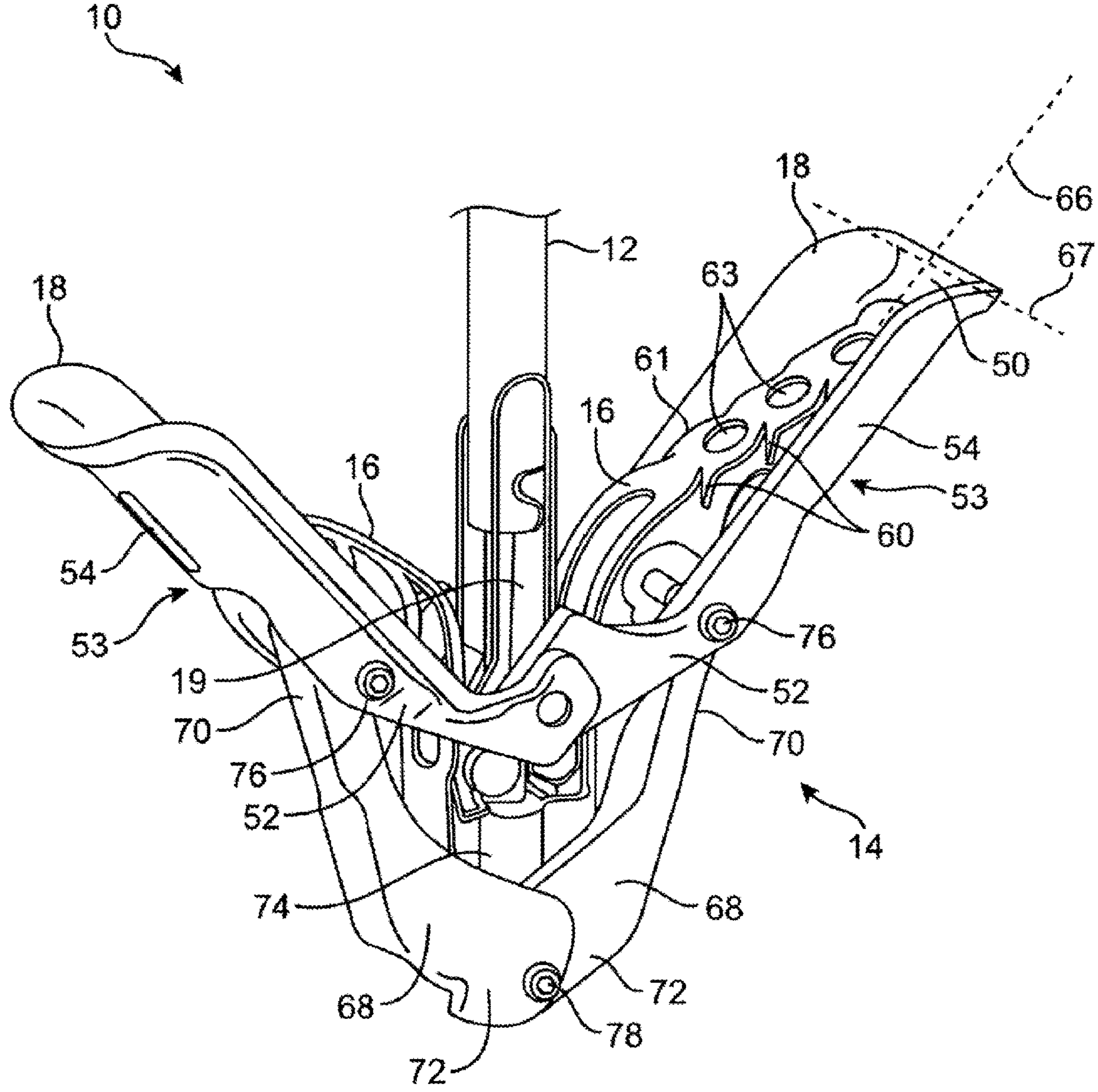
FIGS. 3-7B illustrate an embodiment of a repair device in various positions that may be utilized during deployment of the repair device.

FIG. 3 illustrates a more detailed view of the repair device 14. Here, the repair device 14 is shown coupled to a shaft 12 to form an interventional device 10. The repair device 14 includes a coupling member 19 and a pair of opposed distal elements 18. The distal elements 18 comprise elongate arms 53, each arm having a proximal end 52 rotatably connected to the coupling member 19 and a free end 54. In this embodiment, the free ends 54 have a rounded shape to minimize interference with and trauma to surrounding tissue structures. Preferably, each free end 54 defines a curvature about two axes, one being a longitudinal axis 66 of arms 53. Thus, engagement surfaces 50 have a cupped or concave shape to surface area in contact with tissue and to assist in grasping and holding the valve leaflets. This further allows arms 53 to nest around the shaft 12 in a closed position to minimize the profile of the device during delivery (e.g. transcatheter delivery).

Preferably, arms 53 are at least partially cupped or curved inwardly about their longitudinal axes 66. In the illustrated embodiment, each free end 54 also defines a curvature about an axis 67 perpendicular to longitudinal axis 66. The longitudinal edges of the free ends 54 may flare outwardly. The curvature and/or flaring may function to minimize trauma to the tissue engaged against the distal elements 18. The arms 53 may further include a plurality of openings to enhance grip and to promote tissue ingrowth following implantation.

The valve leaflets are grasped between the distal elements 18 and proximal elements 16. In the illustrated embodiment, the proximal elements 16 are formed as flexible and resilient members cantilevered from coupling member 19. The proximal elements 16 are biased toward the distal elements 18. Each proximal element 16 is shaped and positioned to be at least partially recessed within the concavity of the distal element 18. When the repair device 14 is in an open position, the proximal elements 16 are shaped such that each proximal element 16 is separated from the engagement surface 50 near the proximal end 52 of arm 53 and slopes toward the engagement surface 50 near the free end 54 with the free end of the proximal element contacting engagement surface 50, as illustrated in FIG. 3. This shape of the proximal elements 16 accommodates valve leaflets or other tissues of varying thicknesses.

Proximal elements 16 may include a plurality of openings 63 and/or scalloped edges 61 to increase grip on tissue. The proximal elements 16 may include additional or alternative frictional accessories, frictional features, or grip-enhancing elements to assist in grasping and/or holding the leaflets. In preferred embodiments, the frictional accessories comprise barbs 60 having tapering pointed tips extending toward engagement surfaces 50. Additionally, or alternatively, other frictional accessories may be used, such as prongs, windings, bands, barbs, grooves, channels, bumps, surface roughening, sintering, high-friction pads, coverings, coatings, or a combination of these.

Some embodiments include one or more magnets in the proximal and/or distal elements. For example, the mating surfaces may be made from or may include material of opposite magnetic charge to cause attraction by magnetic force. For example, the proximal elements and distal elements may each include magnetic material of opposite charge so that tissue is held under constant compression between the proximal and distal elements to facilitate faster healing and ingrowth of tissue. Also, the magnetic force may be used to draw the proximal elements 16 toward the distal elements 18, in addition to or alternative to biasing of the proximal elements 16 toward the distal elements 18. In another example, the distal elements 18 each include magnetic material of opposite charge so that tissue positioned between the distal elements 18 is held therebetween by magnetic force (e.g., when the repair device 14 is moved to a closed position).

The illustrated repair device 14 also includes an actuation mechanism. In this embodiment, the actuation mechanism comprises two link members or legs 68, each leg 68 having a first end 70 which is rotatably joined with one of the distal elements 18 at a joint 76 (e.g., riveted, pinned, or otherwise rotatably fastened) and a second end 72 which is rotatably joined with a stud 74. The legs 68 are preferably comprised of a rigid or semi-rigid metal or polymer such as a cobalt chromium alloy (e.g., Elgiloy®) or stainless steel; however, any suitable material may be used. While in the embodiment illustrated both legs 68 are pinned to stud 74 by a single rivet 78, in other embodiments, each leg 68 may be individually attached to the stud 74 by a separate rivet, pin, or other fastening structure. The stud 74 is joinable with an actuator rod which extends through the shaft 12 and is axially extendable and retractable to move the stud 74 and therefore the legs 68 to rotate the distal elements 18 between closed, open, and inverted positions. Likewise, immobilization of the stud 74 holds the legs 68 in place and therefore holds the distal elements 18 in a desired position.

In any of the embodiments of repair device 14 disclosed herein, it may be desirable to provide some mobility or flexibility in distal elements 18 and/or proximal elements 16 in the closed position to enable these elements to move or flex with the opening or closing of the valve leaflets. This provides shock absorption and thereby reduces force on the leaflets and minimizes the possibility for tearing or other trauma to the leaflets. Such mobility or flexibility may be provided by using a flexible, resilient metal or polymer of appropriate thickness to construct the distal elements 18. Further, the distal elements 18 can be connected to the coupling mechanism 19 by a mechanism that biases the distal element into the closed position (inwardly) but permits the arms to open slightly in response to forces exerted by the leaflets. For example, rather than being pinned at a single point, these components may be pinned through a slot that allowed a small amount of translation of the pin in response to forces against the arms. A spring is used to bias the pinned component toward one end of the slot.

Figure 4A:
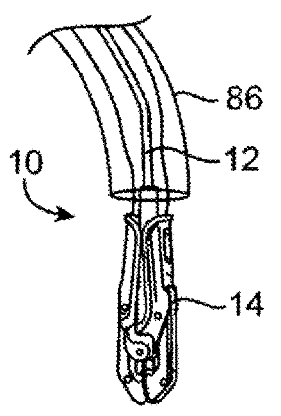

FIGS. 4A-7B illustrate embodiments of the repair device 14 in various positions which may be utilized during delivery and deployment of the device 14. FIG. 4A illustrates an embodiment of an interventional device 10 delivered through a catheter 86. The interventional device 10 includes a repair device 14 coupled to a shaft 12. The repair device 14 is shown in a closed position. FIG. 4B illustrates an expanded view of the repair device 14 in the closed position. As shown, the opposed pair of distal elements 18 are positioned so that the engagement surfaces 50 face each other. Each distal element 18 includes an elongate arm 53 having a cupped or concave shape so that together the arms 53 surround the shaft 12 on opposite sides of the shaft. This provides a low profile for the repair device 14 so as to be readily passable through the catheter 86, other delivery structures, and through any anatomical structures along the delivery path, such as the mitral valve.

Figure 4B:
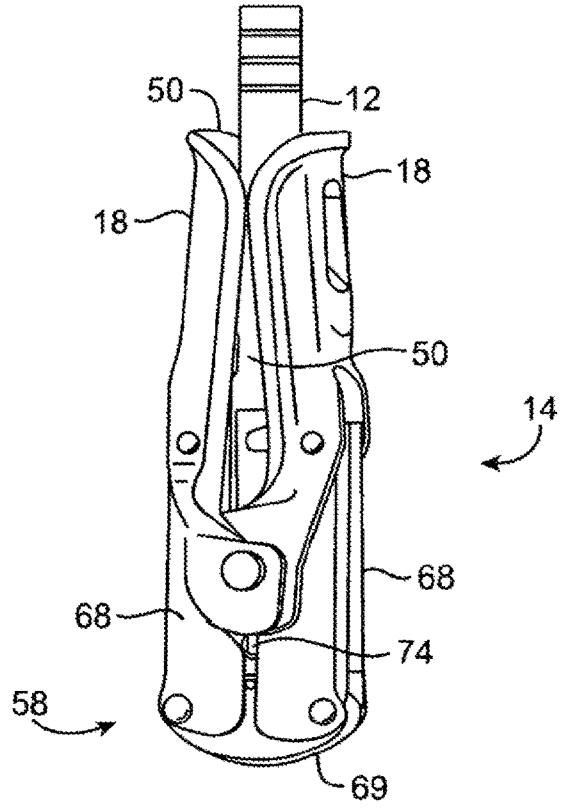

FIG. 4B illustrates an actuation mechanism 58, including two legs 68 which are each movably coupled to a base 69. The base 69 is joined with an actuator rod 64 (see FIG. 6B) which extends through the shaft 12 and is used to manipulate the repair device 14. In some embodiments, the actuator rod 64 attaches directly to the actuation mechanism 58, particularly the base 69. The actuator rod 64 may alternatively attach to a stud 74 which in turn is attached to the base 69. In some embodiments, the stud 74 is threaded so that the actuator rod 64 attaches to the stud 74 through threaded engagement. Alternatively, the rod 64 and stud 74 may be joined by another releasable mechanism (e.g., a mechanism including one or more clips, slots, tabs, pins, other mechanical fastener components, magnetic components) to allow the repair device 14 to be detached from shaft 12.

Figure 5A:
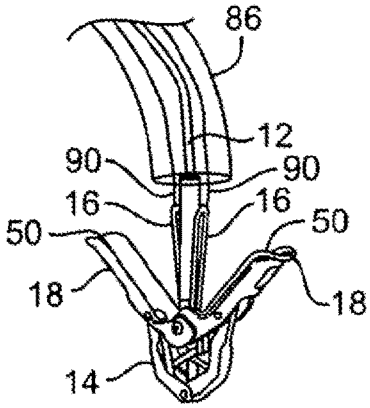
Figure 5B:
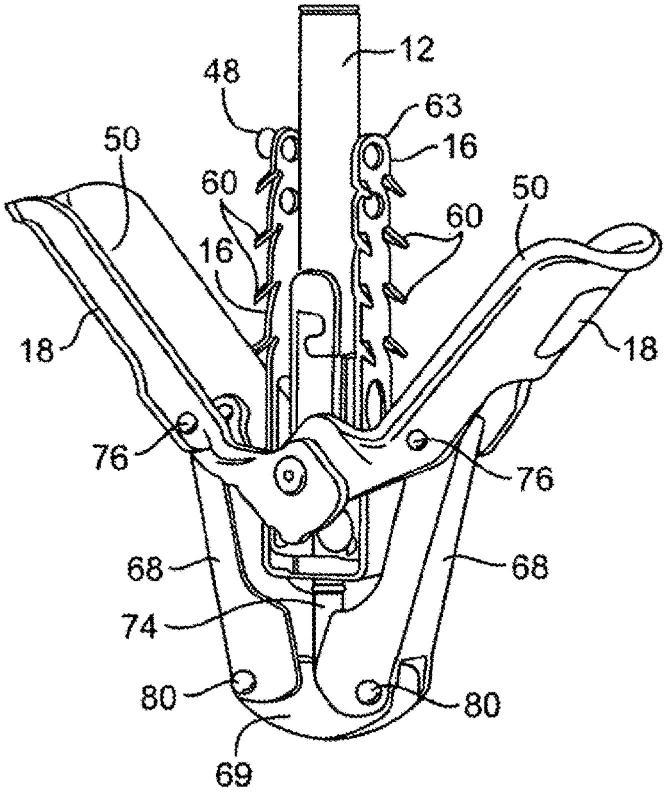

FIGS. 5A-5B illustrate the repair device 14 in an open position. In the open position, the distal elements 18 are outwardly rotated so that the engagement surfaces 50 face a first direction. In this embodiment, distal advancement of the stud 74 relative to coupling member 19 by action of the actuator rod 64 applies force to the distal elements 18, which begin to rotate outwardly around joints 76 due to freedom of movement in this direction. The outward movement of the distal elements 18 causes rotation of the legs 68 about joints 80 so that the legs 68 are directly slightly outwards. The stud 74 may be advanced to any desired distance correlating to a desired outward separation of the distal elements 18 (e.g., typically between about 90 and 180 degrees apart from each other on the proximal side).

Proximal elements 16 are typically biased outwardly toward arms 53. The proximal elements 16 may be moved inwardly toward the shaft 12 and held against the shaft 12 with the aid of proximal element lines 90 (see FIGS. 5A, 6A, and 7A) which can be in the form of sutures, wires, nitinol wire, rods, cables, polymeric lines, or other suitable structures. The proximal element lines 90 may be connected with the proximal elements 16 by threading the lines 90 through one or more of the proximal elements 16. For example, a line 90 may pass through one or more of the openings 63 in a proximal element 16.

Further, a line loop 48 (or a plurality of such loops) may be present on a proximal element 16, also illustrated in FIG. 5B, through which a proximal element line 90 may pass and double back. Such a line loop 48 may be useful to reduce friction on proximal element line 90 or when the proximal elements 16 are solid or devoid of other loops or openings through which the proximal element lines 90 may attach. A proximal element line 90 may attach to the proximal elements 16 by detachable means, for example, to allow a single line 90 to be attached to a proximal element 16 without doubling back. Examples of such detachable means include hooks, snares, clips, breakable couplings, and the like. By applying sufficient tension to the proximal element line 90, the detachable means may be detached from the proximal element 16 such as by breakage of the coupling.

In the open position, the repair device 14 can engage the tissue which is to be approximated or treated. For example, the illustrated embodiment may be utilized for repair of the mitral valve using an antegrade approach from the left atrium. In some implementations, the interventional device 10 is advanced through the mitral valve from the left atrium to the left ventricle. The distal elements 18 are oriented to be perpendicular to the line of coaptation and then positioned so that the engagement surfaces 50 contact the ventricular surface of the valve leaflets. The proximal elements 16 remain on the atrial side of the valve leaflets so that the leaflets lie between the proximal and distal elements. As explained in more detail below, the proximal elements 16 may then be actuated to move toward the distal elements 18 to grasp the valve leaflets between the distal elements 18 and the proximal elements 16.

Figure 6A:
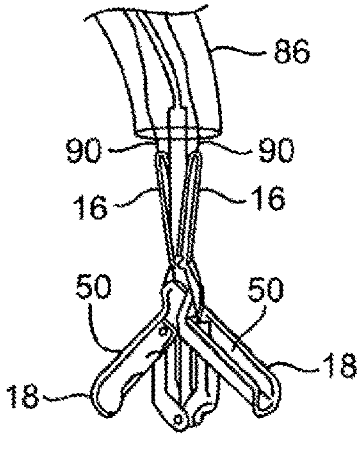
Figure 6B:
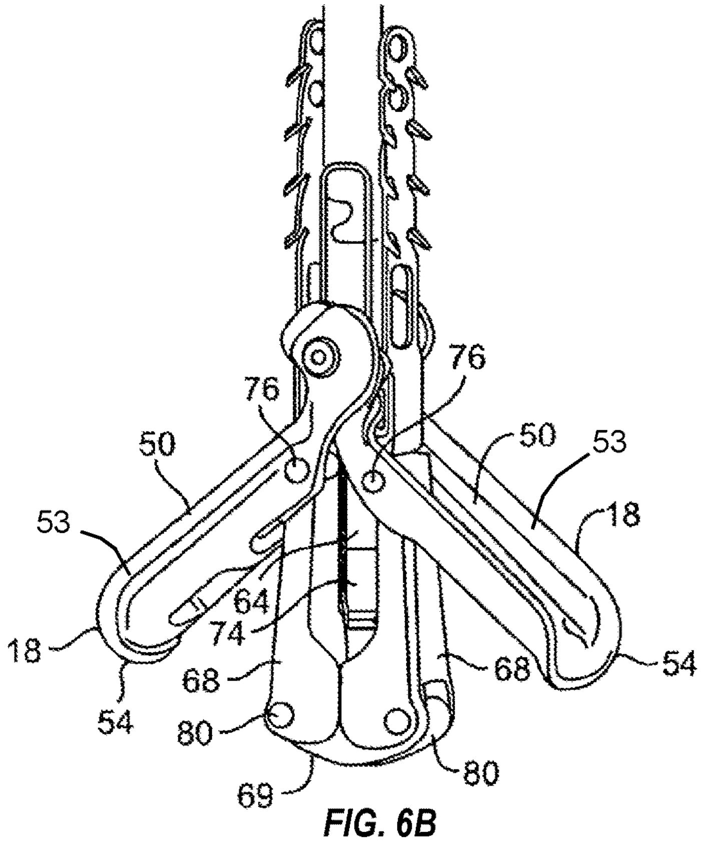

In some circumstances, it may be desired to invert the repair device 14 to aid in repositioning or removal of the repair device 14. FIGS. 6A-6B illustrate the repair device 14 in the inverted position. An inverted position may be achieved by further advancement of stud 74 relative to coupling member 19 so that the distal elements 18 are further rotated until each arm 53 forms an obtuse angle relative to shaft 12 (e.g., forming an angle between arms 53 of about 270 to 360 degrees). Further advancement of the stud 74 further rotates the distal elements 18 around joints 76. This rotation and movement of the distal elements 18 causes rotation of the legs 68 about joints 80 so that the legs 68 are returned toward their initial position, generally parallel to each other.

The inverted position allows withdrawal of the repair device 14 through a targeted valve while minimizing trauma to the leaflets. Engagement surfaces 50 provide an atraumatic surface for deflecting tissue as the repair device is retracted proximally. In the illustrated embodiment, barbs 60 are angled slightly in the distal direction (away from the free ends of the proximal elements 16), reducing the risk that the barbs 60 will catch on or lacerate tissue as the repair device is withdrawn.

Figure 7A:
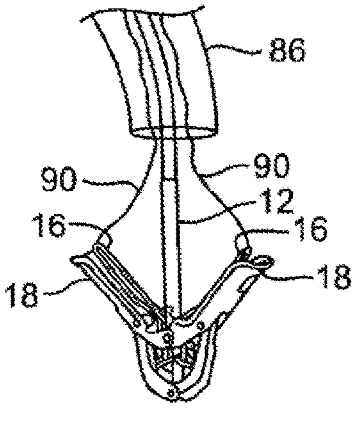
Figure 7B:
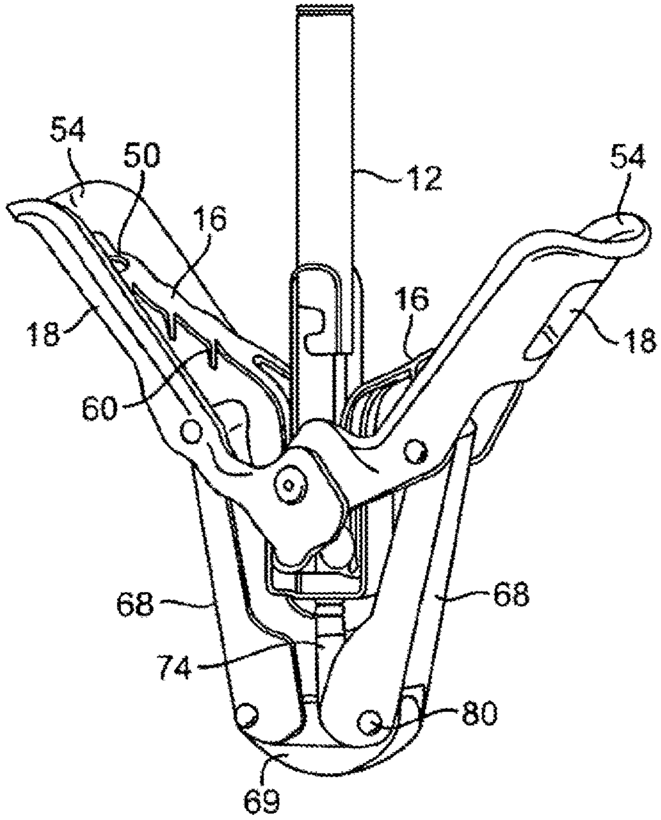

Once the repair device 14 has been positioned in a desired location against the valve leaflets, the leaflets may then be captured between the proximal elements 16 and the distal elements 18. FIGS. 7A and 7B illustrate the repair device 14 in such a position. Here, the proximal elements 16 are lowered toward the engagement surfaces 50 so that the leaflets are held therebetween. In FIG. 7B, the proximal elements 16 are shown to include barbs 60 which may be used to provide enhanced gripping of the leaflets. This position is similar to the open position of FIGS. 5A and 5B, but with the proximal elements 16 lowered toward arms 53 by releasing tension on proximal element lines 90. The proximal elements 16 may be raised and the distal elements 18 adjusted or inverted to reposition the repair device 14.

After the leaflets have been captured between the proximal and distal elements 16 and 18 in a desired arrangement, the distal elements 18 may be locked to hold the leaflets in this position or the repair device 14 may be returned to or toward a closed position.

FIGS. 8-14 illustrate other embodiments of repair devices having one or more adjustable arms, the repair devices being configured for enhanced grasping and/or approximating of tissues in an interventional procedure, such as for grasping mitral valve leaflets in a mitral valve repair procedure. The various exemplary embodiments illustrated in FIGS. 8-14 may include one or more of the components/features of the embodiments illustrated in FIGS. 1A-7B. For example, the features related to manipulation or actuation of the distal and proximal elements, relative positioning of the distal and proximal elements, structure and shape of the distal and proximal elements, delivery, deployment, and decoupling of the repair device, and/or other features may be combined with or incorporated into any of the embodiments of FIGS. 8-14. For purposes of clarity, the distinguishing features of the embodiments of FIGS. 8-14 will be the focus of the following description; however, it will be understood that the related description of FIGS. 1A-7B is also applicable.

Figure 8:
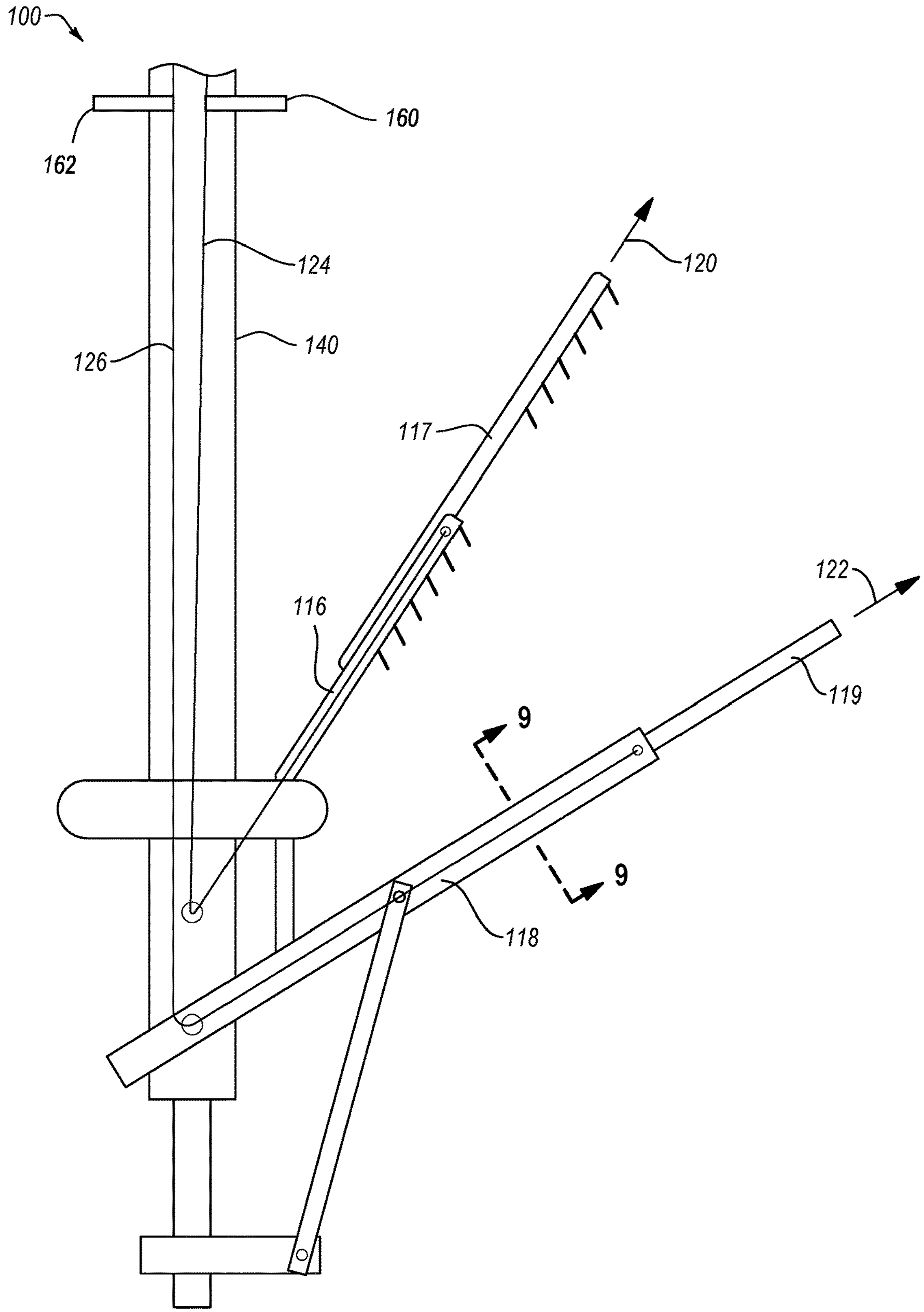
FIG. 8 illustrates another embodiment of a repair device having adjustable arms enabling linear extension and retraction of the arms to adjust arm length.

FIG. 8 illustrates an embodiment of a repair device 100 including a proximal element 116 having a proximal adjustable arm 117 and a distal element 118 having a distal adjustable arm 119. For purposes of clarity, the depiction of FIG. 8 shows only one proximal element 116 and one distal element 118. It will be understood that additional elements may be disposed opposite the illustrated proximal element 116 and distal element 118, as with other embodiments described herein. For example, an additional proximal element may be disposed opposite the illustrated proximal element 116 on an opposite side of the shaft 140. Further, an additional distal element may be disposed opposite the illustrated distal element 118 on an opposite side of the shaft 140, resulting in a configuration of two distal elements and two corresponding proximal elements, as with the embodiments shown in FIGS. 1A-7B.

As indicated by arrow 120, the proximal element 116 is associated with a proximal arm 117 configured to be outwardly extendable away from a base of the proximal element 116 (the portion of the proximal element 116 closest to the shaft 140). In addition, as indicated by arrow 122, the distal element 118 is associated with a distal arm 119 configured to be outwardly extendable away from a base of the distal element 118 (the portion of the distal element 118 closest to the shaft 140). The distal element 118 and the proximal element 116 may be manipulated and positioned as described above in relation to the proximal and distal elements 16 and 18 of the embodiments of FIGS. 1A-7B. The embodiment shown in FIG. 8 provides one or more additional advantages by enabling the extension and/or adjustment of the arms 117 and 119.

For example, in a mitral valve repair procedure where the repair device 100 is introduced from an antegrade approach from the atrium, the repair device 100 may be positioned so as to extend through the mitral valve and into the ventricular side of the mitral valve. The repair device 100 may then be moved to an open position (such as the open position shown in FIGS. 5A and 5B) in order to position the distal elements 118 on the ventricular side of the valve leaflets. From the open position, the distal adjustable arm 119 may be actuated so as to move from a retracted position to an extended position, effectively lengthening the reach of the distal element 118. In the extended position, the distal element 118 and arm 119 are able to provide greater structure and surface area for engagement against targeted leaflet tissue. The extended configuration thereby enables easier and/or fuller engagement of the distal element 118 against targeted tissues. Moreover, the extended configuration is provided without also requiring a large profile during the prior delivery, such as would be the case in a device having static (non-extendable) arms of similar extended length.

As shown in FIG. 8, the proximal adjustable arm 117 may also be actuated to move from a retracted position to an extended position, effectively extending the reach of the proximal element 116. For example, the proximal element 116 and arm 117 may be actuated to the extended position prior to release of the proximal element 116 toward the distal element 118 to grasp tissue between the proximal element 116 and distal element 118. An extended proximal element 116 can provide greater structure and surface area for grasping of the targeted tissue and for biasing and compressing against the corresponding distal element 118. In other implementations, retraction of gripping elements, such as retraction of one or more proximal adjustable arms 117, can be used to pull leaflet tissue further into the repair device 100 (i.e., closer to the shaft 140) either before or after closure of the repair device 100. Thus, leaflet positioning and corresponding blood flow dynamics through the targeted valve can be manipulated as desired by retracting and/or extending one or more adjustable arms of the repair device 100.

The embodiment illustrated in FIG. 8 includes a distal element 118 and a proximal element 116 each including respective adjustable arms 117 and 119 configured to extend or retract linearly. As shown, the proximal adjustable arm 117 is configured to extend or retract in a direction parallel to the axis of the proximal element 116, and the distal adjustable arm 119 is configured to extend or retract in a direction parallel to the axis of the distal element 118. In other embodiments, the proximal adjustable arm 117 and/or the distal adjustable arm 119 may be configured so as to extend at an offset angle and/or to extend with a different curvature than the respective proximal or distal elements 116 or 118 from which they extend. For example, the proximal adjustable arm 117 and/or the distal adjustable arm 119 may be formed of a superelastic/shape-memory material that allows alignment with the respective proximal or distal element 116 or 118 when in a retracted position and allows a different curvature to form as it is extended from the respective proximal or distal element 116 or 118.

The illustrated embodiment includes both a proximal adjustable arm 117 and a distal adjustable arm 119, providing the ability to extend and retract both the proximal element 116 and the distal element 118. Other embodiments may include a different number of adjustable elements. For example, in a typical embodiment having four gripping elements (two distal elements and two corresponding proximal elements), 1 to 4 of the gripping elements may be configured with adjustable arm functionality as described herein. In one example, all (e.g., two) of the distal elements include length-adjustable arms, whereas the proximal elements are length static. In another example, all (e.g., two) of the proximal elements include length-adjustable arms, whereas the distal elements are length static. In another example, one corresponding pair of a distal element and a proximal element include length-adjustable arms so as to enable adjustment to grasp tissue therebetween, whereas the other corresponding distal and proximal element pair are configured with static lengths.

In the illustrated embodiment and in other examples described herein, two arm segments are provided (e.g., the proximal element 116 and proximal arm 117 make up the two segments for the particular proximal arm structure). In other embodiments, additional segments may be included as well, such as by attaching additional arm segments in series to provide additional points of extension control. For example, some embodiments may include additional adjustable segments operatively coupled to a primary adjustable segment, which itself is operatively coupled to the element closest to the shaft, thereby providing additional points of adjustability and even more granular adjustability.

In the illustrated embodiment, extension and retraction of the proximal adjustable arm 117 is controllable by control line 124, and extension and retraction of the distal adjustable arm 119 is controllable by control line 126. As explained in greater detail below, in some embodiments, one or more of the adjustable arms are biased outward toward the extended position. For example, the proximal adjustable arm 117 may be coupled to the corresponding control line 124 such that tensioning of the control line 124 pulls the arm 117 into the retracted position. Because the adjustable arm 117 is biased toward the extended position (e.g., through one or more coil or leaf springs), release of tension in control line 124 allows the adjustable arm 117 to move toward the extended position. The adjustable arm 117 may be retracted upon re-tensioning of the corresponding control line 124. The distal adjustable arm 119 may be configured so as to operate in a similar manner upon manipulation of corresponding control line 126.

The illustrated embodiment also includes a pair of harness members 160 and 162 operatively connected to control lines 124 and 126, respectively. The harness members 160 and 162 may provide a convenient mechanism for readjusting the adjustable arms of the repair device 100, such as in a touch up procedure subsequent to the initial deployment (e.g., typically before about 60 days post deployment). As described above, some patients may experience refractory symptoms, such as persisting regurgitation or overly high pressure gradients, at time points after the initial procedure and deployment. The harness members 160 and 162 provide a mechanism by which a physician can adjust the adjustable arms 117 and/or 119. For example, a simple snare or other pulling device capable of engaging with a harness member 160 and/or 162 can then be utilized to manipulate the engaged harness member to adjust the repair device as desired. One or more harness members 160, 162 may include radiopaque markers and/or may include a radiopaque material to provide visualization during such an adjustment procedure. In other embodiments, one or more harness members may be configured as hooks, magnetic couplings, snare loops, or other structures that can be engaged with to enable manipulation of the structures. Although the illustrated harness members 160 and 162 are illustrated as being operatively coupled to respective control wires, other embodiments may include, in addition to or as an alternative, one or more harness members coupled directly to an extendable arm. Such embodiments can be subsequently adjusted by engaging with the harness and directly manipulating the corresponding adjustable arm.

Figure 9:
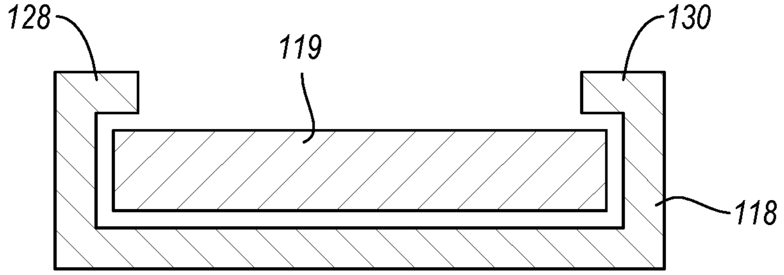
FIG. 9 illustrates a cross-sectional view of a gripping element and associated adjustable arm of the repair device of FIG. 8.

FIG. 9 illustrates a cross-sectional view of the distal element 118 taken along the line 9-9 shown in FIG. 8. Although the components depicted in FIG. 9 are associated with the distal element 118 and distal adjustable arm 119, the description may be applied to the proximal element 116 and proximal adjustable arm 117 as well. For example, any of the following description related to FIG. 9 describing the distal element 118, the distal adjustable arm 119, and the relationship between the distal element 118 and the distal adjustable arm 119 may be considered as also describing the proximal element 116, the proximal adjustable arm 117, and the relationship between the proximal element 116 and the proximal adjustable arm 117.

In the illustrated embodiment, the distal adjustable arm 119 is positioned within the distal element 118 so as to be translatable relative to the distal element 118. As shown, the distal element 118 is configured as a track with edges 128 and 130 functioning to hold the distal adjustable arm 119 in position against the distal element 118 with respect to two axes while allowing translation of the distal adjustable arm 119 along the intended extension/retraction axis. In the illustrated embodiment, the distal element 118 partially encloses the corresponding distal adjustable arm 119. In other embodiments, the adjustable arm may be fully enclosed. For example, the edges 128 and 130 may be brought together so as to fully enclose the adjustable arm 119.

In the illustrated embodiment, the cross-sectional shape of the distal adjustable arm 119 is substantially rectangular, and the distal element 118 includes a corresponding cross-sectional shape. In other embodiment, the cross-sectional shapes of the adjustable arm and gripping element may be circular, ovoid, curved (as in the embodiment shown in FIGS. 3-7B) irregular, polygonal, or a combination thereof (e.g., a different cross-sectional shape along different sections of length of the gripping element and arm). In the illustrated embodiment, the adjustable arm 119 is enclosed or at least partially enclosed by the distal element 118 so that the adjustable arm 119 extends out of and retracts into the distal element 118. In other embodiments, the relative cross-sectional shapes and positions are essentially reversed so that the adjustable arm translates along an inwardly disposed gripping element, the gripping element functioning as an inwardly disposed track for the surrounding or partially surrounding adjustable arm. In other embodiments, a distal element 118 and an adjustable arm 119 may be positioned side by side, with one side configured to extend relative to the other static side.

Figure 10:
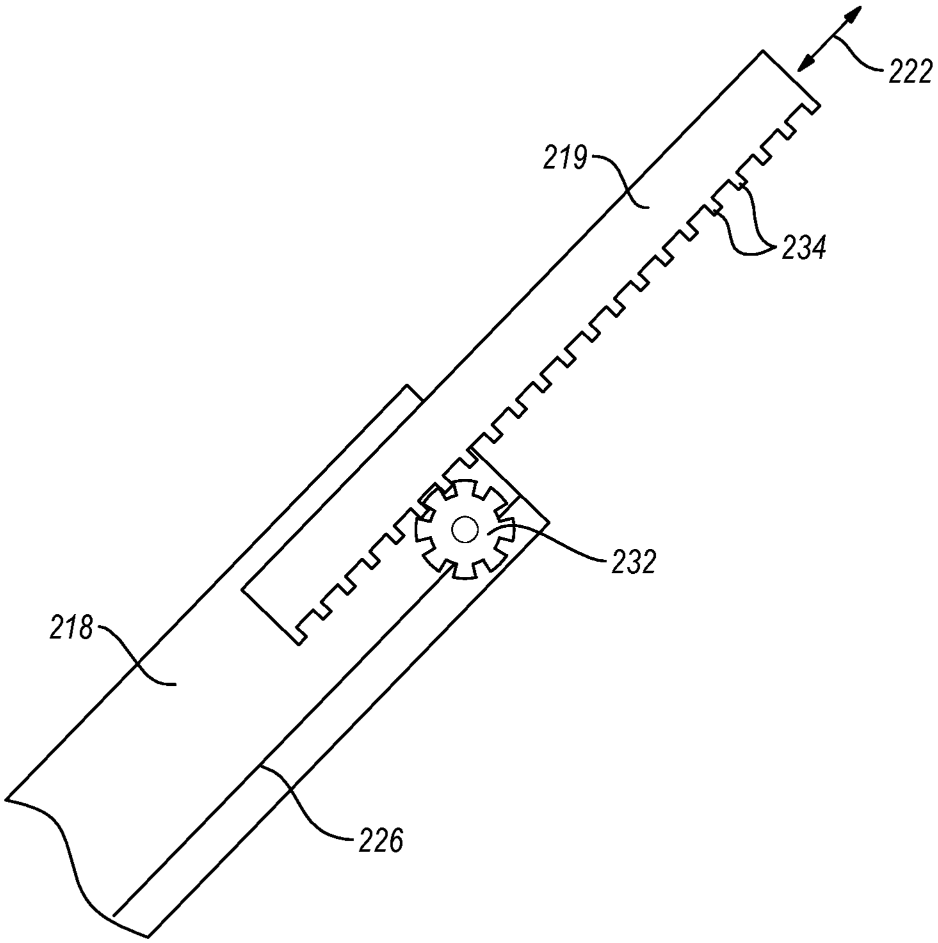
FIG. 10 illustrates a cross-sectional view of a gripping element and associated adjustable arm showing an exemplary gear-based mechanism for controlling the extension and retraction of the adjustable arm.

FIG. 10 illustrates a cross-sectional view of a gripping element 218 and an associated adjustable arm 219 showing one example for controlling the extension/retraction of the adjustable arm 219. The gripping element 218 may represent a proximal element and/or a distal element of any of the repair device embodiments described herein (e.g., the repair device 100 shown in FIG. 8). As shown, the adjustable arm 219 includes a plurality of teeth 234 enabling the adjustable arm 219 to engage with a corresponding gear 232 of the gripping element 218. In this embodiment, at least a portion of the adjustable arm 219 is configured as a gear rack associated with corresponding gear 232 so that rotation of the gear 232 controls linear movement (extension and retraction) of the adjustable arm 219, as indicated by arrow 222.

In the illustrated embodiment, rotation of the gear 232 is controlled by control line 226. For example, the control line 226 may be tied or coupled to a corresponding gear shaft so that movement of the control line 226 rotates the gear 232. Additionally, or alternatively, a gear may be manipulated through one or more additional gears, connecting shafts, and/or other components of a gear assembly. Other embodiments may include, additionally or alternatively, one or more belt and pulley assemblies, sprocket and chain assemblies, and/or other force transmitting assemblies configured to provide control over linear movement of the adjustable arm 219.

Figure 11:
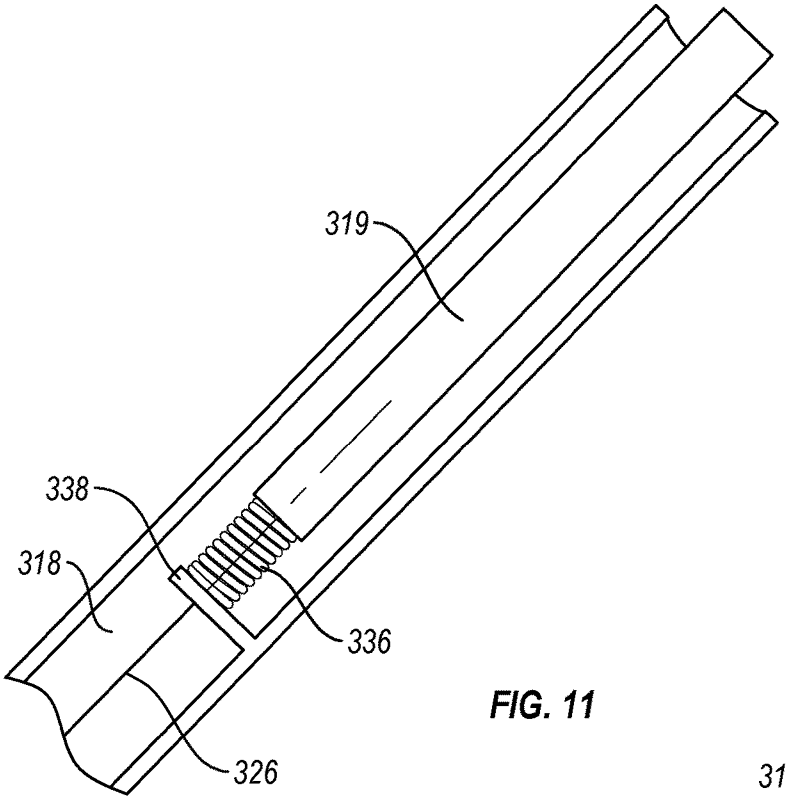
FIGS. 11 and 12 illustrate a cross-sectional view of another embodiment of a gripping element and associated adjustable arm showing an exemplary spring-based mechanism for controlling the extension and retraction of the adjustable arm.
Figure 12:
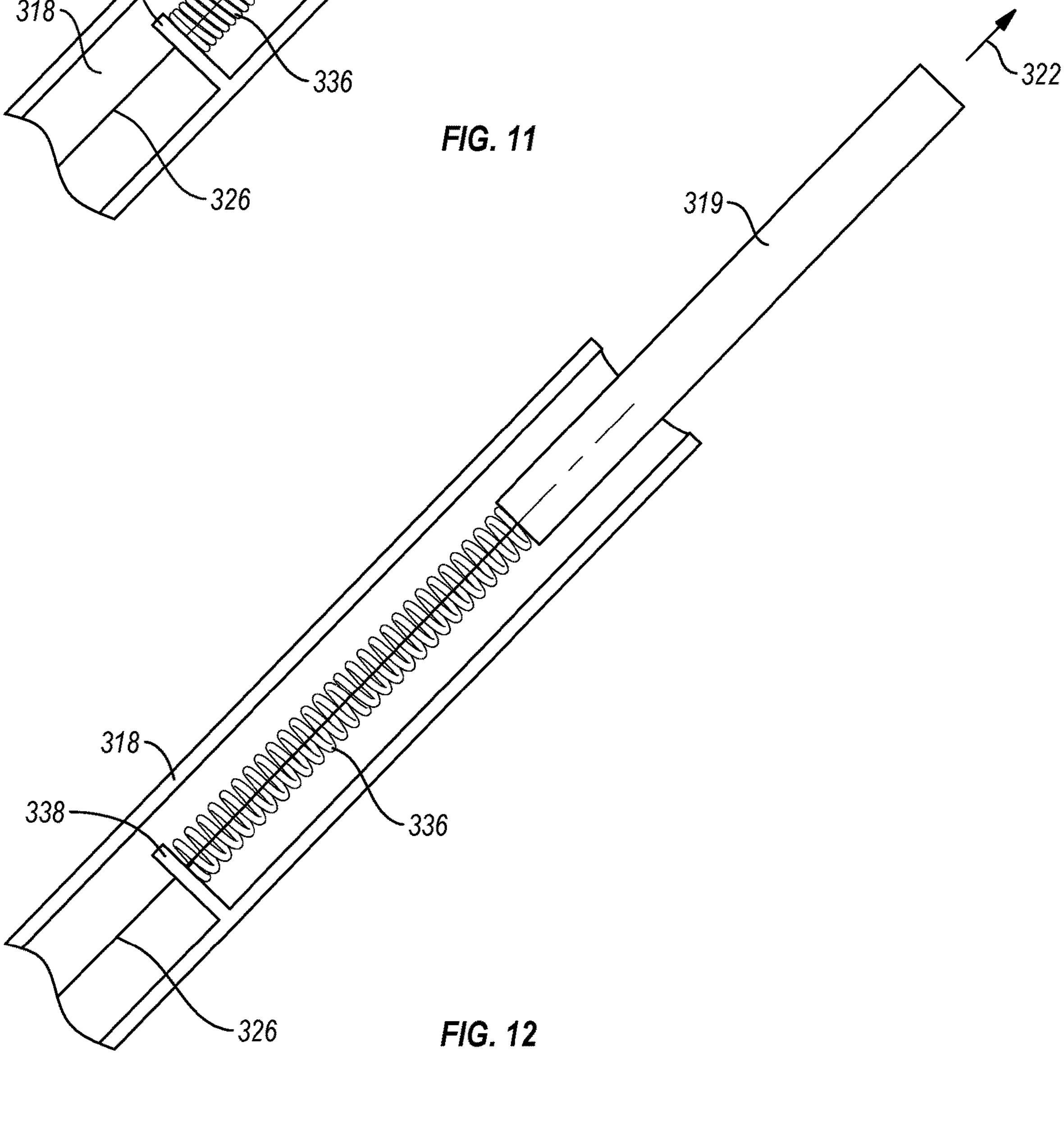

FIGS. 11-12 illustrate another embodiment of a gripping element 318 and an associated adjustable arm 319. The gripping element 318 may represent a proximal element and/or a distal element of any of the repair device embodiments described herein (e.g., the repair device 100 shown in FIG. 8). As shown, the illustrated embodiment includes a spring 336 positioned between the adjustable arm 319 and a stop 338 so as to provide a force biasing the adjustable arm outwards toward an extended position. FIG. 11 illustrates the adjustable arm 319 in a retracted position, and FIG. 12 illustrates the adjustable arm 319 moving toward an extended position, as indicated by arrow 322.

FIG. 11 shows the adjustable arm 319 held in the retracted position, against the spring 336, by tensioning a control line 326. The control line 336 is coupled to a medial side (i.e., the side closest to the longitudinal axis of the repair device) of the adjustable arm 319 to allow the adjustable arm 319 to be manipulated by adjusting tension in the control line 326. FIG. 12 shows the adjustable arm 319 moving toward an extended position. As tension in the control line 326 is released, the biasing force caused by expansion of the spring 336 pushes the adjustable arm 319 outward, as indicated by arrow 322.

Figure 13:
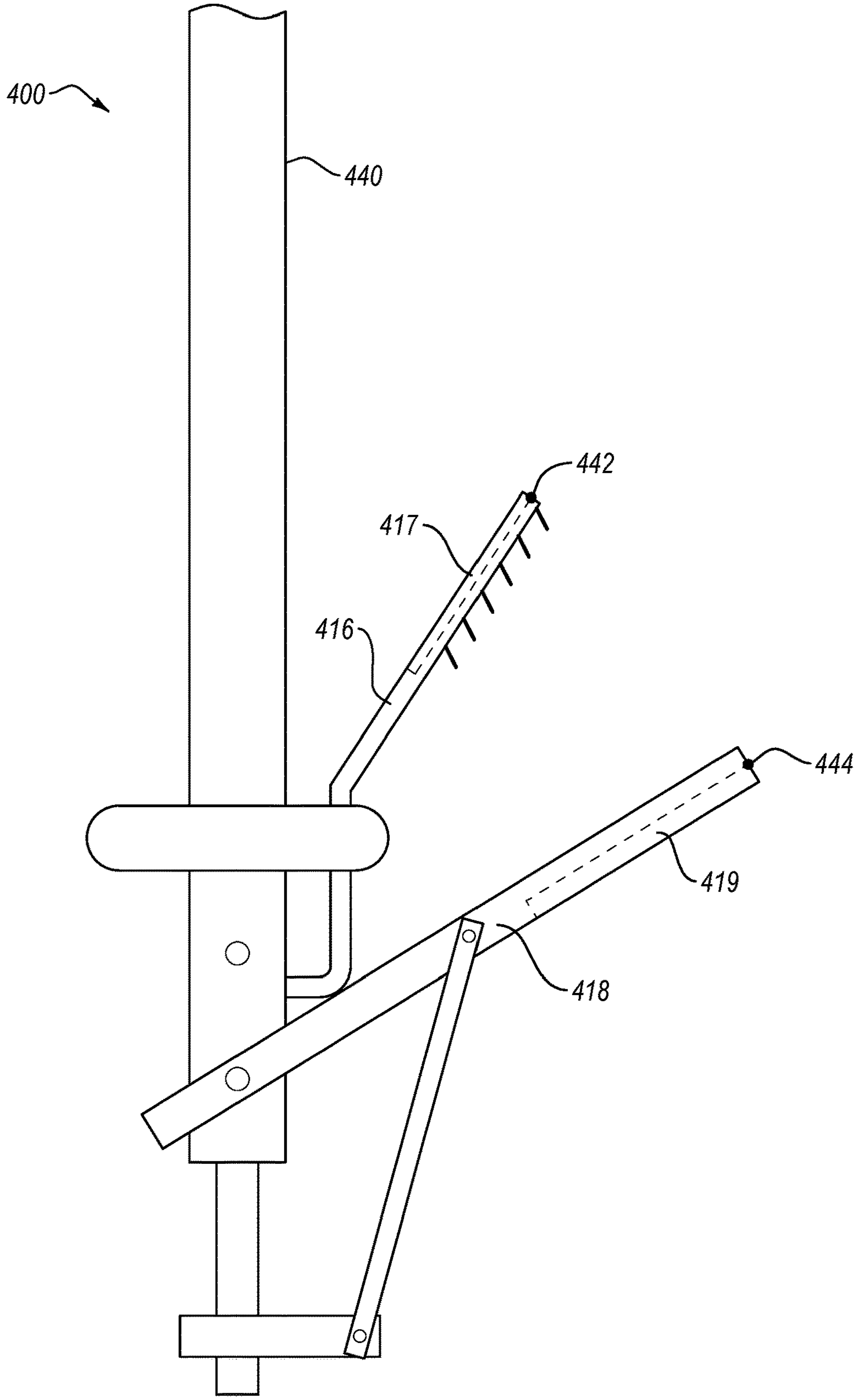
FIGS. 13 and 14 illustrate another embodiment of a repair device having adjustable arms enabling rotatable extension and retraction of the arms to adjust arm length.
Figure 14:
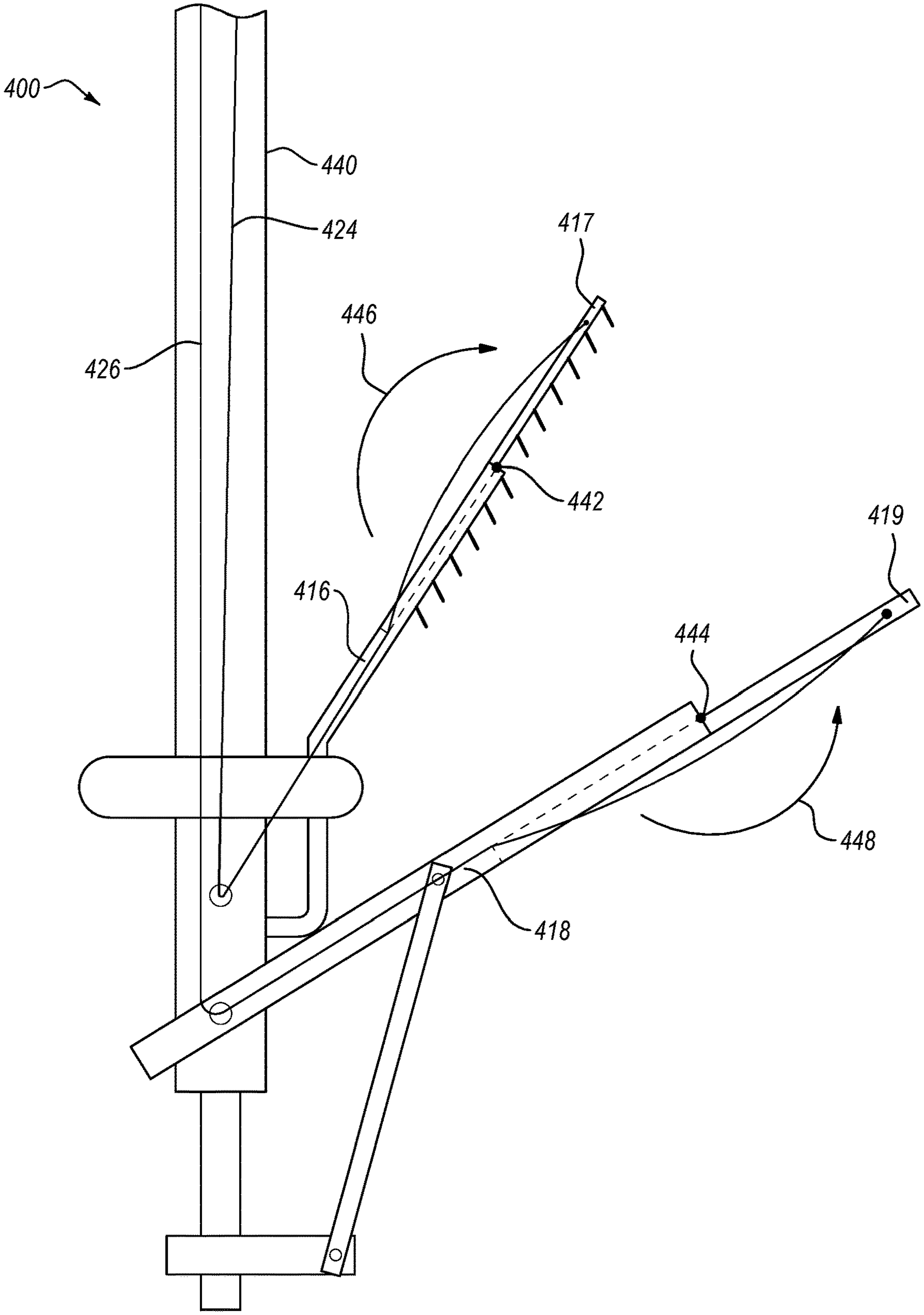

FIGS. 13 and 14 illustrate another embodiment of a repair device 400 having adjustable arms. The repair device 400 may be configured similarly to the repair device 100 shown in FIG. 8, having similar components, features, and functionality. However, in the illustrated embodiment, a proximal adjustable arm 417 and a distal adjustable arm 419 are configured so as to be capable of moving between a retracted position and an extended position by rotating about hinges 442 and 444, respectively. As with the embodiment shown in FIG. 8, a single proximal element 416 and a single distal element 418 are shown for clarity. However, it will be understood that one or more additional proximal elements or distal elements may be included. Typically, an embodiment includes a pair of distal elements each on opposite sides of the shaft 440 and a pair of corresponding proximal elements each on opposite sides of the shaft 440.

FIG. 13 shows the repair device 400 with the proximal adjustable arm 417 in a retracted position (shown in dashed lines) against the proximal element 416, and the distal adjustable arm 419 in a retracted position (shown in dashed lines) against the distal element 418. FIG. 14 illustrates the proximal adjustable arm 417 and the distal adjustable arm 419 moved into extended positions. As shown, the proximal adjustable arm 417 is rotated about hinge 442 and the distal adjustable arm 419 is rotated about the hinge 444.

In the illustrated embodiment, the proximal adjustable arm 417 is configured to rotate about the hinge 442 on a superior side of the proximal element 416, as indicated by arrow 446, and the distal adjustable arm 419 is configured to rotate about the hinge 444 on an inferior side of the distal element 418, as indicated by arrow 448. In other embodiments, the proximal adjustable arm 417 and/or the distal adjustable arm 419 may be configured to rotate about an opposite side from that depicted in FIG. 14. However, in embodiments intended for use in cardiac valve repair procedures, the depicted configuration is preferred.

For example, during deployment at a cardiac valve, such as a mitral valve, the distal element 418 may be positioned on a ventricular side of the valve before deploying the distal adjustable arm 419. By configuring the adjustable arm 419 to rotate about an inferior side of the distal element 418, the adjustable arm 419 is able to effectively extend the length of the distal element 418 without being prevented from rotating by the leaflets or other valve structures located on the superior side of the distal element 418. Likewise, the proximal adjustable arm 417 is configured to rotate about a superior side of the proximal element 416 so as to effectively extend the length of the proximal element 416 without being prevented from rotating by the valve structures located on the inferior side of the proximal element 416.

The embodiment of FIGS. 13 and 14 includes a proximal adjustable arm 417 and a distal adjustable arm 419. Other embodiments may include a combination of static length gripping elements and gripping elements having adjustable arms. For example, some embodiments may include a pair of distal elements each having adjustable arms and a pair of corresponding proximal elements that omit adjustable arms (e.g., are static in length). Other embodiments may include additional numbers or combinations of elongating and/or pivoting arm components, such as those described herein, attached in series to provide even further extension and/or to provide more extension control points for more granular control over arm extension.

In the illustrated embodiment, control over the proximal adjustable arm 417 is provided by control line 424, and control over the distal adjustable arm 419 is provided by control line 426. For example, the hinges 442 and 444 may be configured as torsion springs to bias the adjustable arms 417 and 419 toward the extended position. As shown, the control lines 424 and 426 are attached to the respective adjustable arms 417 and 419 (e.g., at lateral sections of the adjustable arms) such that the application of tension to the control lines 424 and 426 causes the respective adjustable arms 417 and 419 to rotate towards the retracted position, and such that release of tension allows the respective adjustable arms 417 and 419 to rotate outwardly according to the biasing force.

Figure 15A:
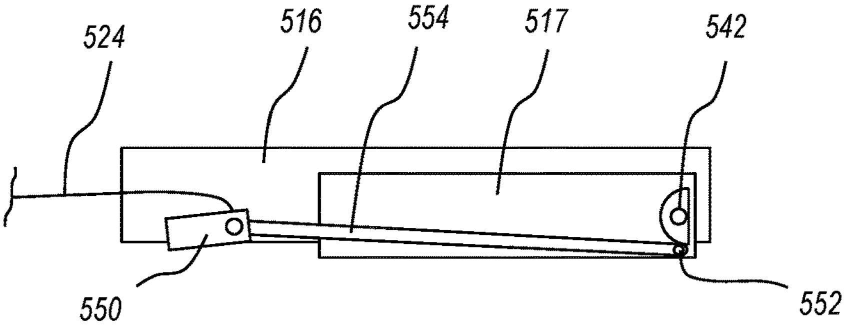
FIGS. 15A to 15C illustrate an embodiment of another mechanism for controlling extension and retraction of an adjustable arm.
Figure 15B:
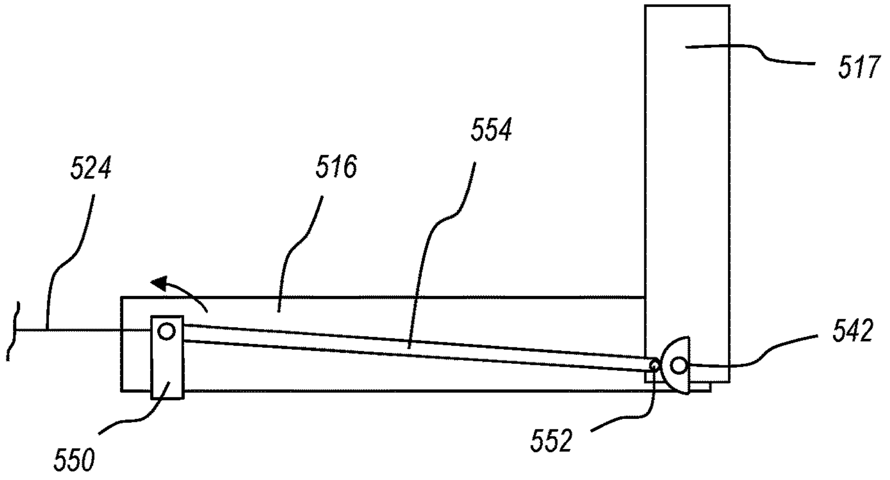
Figure 15C:
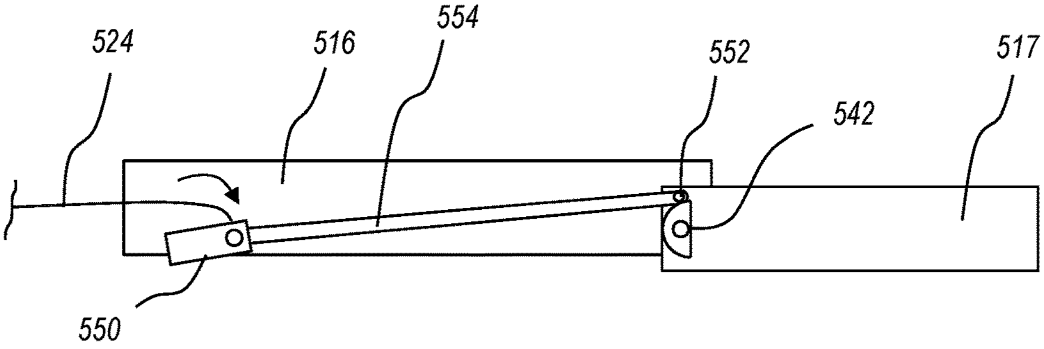

FIGS. 15A to 15C illustrate another embodiment of a mechanism for controlling extension and retraction of one or more adjustable arms. The illustrated embodiment may be utilized with any of the repair device embodiments described herein. For convenience and clarity, other portions of the repair device (e.g., shaft, additional arms) are not shown in these views. The illustrated adjustment mechanism is shown in the context of a proximal element 516 and corresponding proximal adjustable arm 517; however, it will be understood that the same principles may be applied to the adjustment of a distal element and corresponding distal adjustable arm.

FIG. 15A shows the adjustable arm 517 in a retracted position. The adjustable arm is rotatable about hinge 542 to move between the retracted position and the extended position. The illustrated embodiment also includes a lever 550 coupled to a lever arm 554. As shown, the lever arm 554 extends from the lever 550 to a pivot joint 552 disposed near the hinge 542. The adjustable arm 517 is pivotally coupled to the lever arm 554 at the pivot joint 552. The lever 550 may be operatively coupled to a control line 524, as shown. The application or release of tension in the control line 524 controls actuation of the lever 550.

FIG. 15B illustrates a transition position between the retracted position shown in FIG. 15A and the extended position shown in FIG. 15C. As shown in FIG. 15B, the lever 550 has been moved medially from the adjustable arm 517 (e.g., through an increase in tension in control line 524). The movement of the lever 550 is transferred to the lever arm 554, which in turn moves the pivot joint 552 to which the adjustable arm 517 is connected. As the pivot joint 552 moves relative to the hinge 542, the adjustable arm 517 rotates about hinge 542, thereby moving away from the element 516 and toward the extended position.

FIG. 15C illustrates the adjustable arm 517 in the extended position. From the position shown in FIG. 15B, the lever 550 is shown as moving back down to move the lever arm 554 laterally forward. As the lever arm 554 moves, the pivot joint 552 continues to rotate along the rotation path started when moving from the retracted position of FIG. 15A to the transition position shown in FIG. 15B. Because the pivot joint 552 couples the lever arm 554 to the adjustable arm 517, the continued rotation of the pivot joint 552 further rotates the adjustable arm 517 until the adjustable arm is in the extended position as shown.

In the illustrated embodiment, the hinge 542 includes a curved cam surface. The cam surface of the hinge 542 can be utilized to assist in guiding the distal end of the lever arm 554 as it moves the pivot joint 552 around the hinge 542 to move the adjustable arm 517. One or more of the device components may also be configured to provide a spring force, in addition to any intrinsic momentum already occurring during extension/retraction movements, to encourage rotation of the adjustable arm 517 on the curved cam surface of the hinge 542 until full actuation or full retraction is accomplished. For example, the lever 550 can be biased toward the down position shown in FIGS. 15A and 15C so that the adjustable arm 517 will be guided to an appropriate position. Additionally, or alternatively, the surface roughness of the curved cam surface of the hinge 542 can be tuned so as to optimize the balance between reliable actuation of the adjustable arm 517 and avoiding excessive force during arm actuation (e.g., to avoid tissue injury from overly forceful and/or accidental actuation). For example, a relatively smoother cam surface can provide relatively easier actuation and adjustment of the adjustable arm 517, whereas a relatively rougher surface can limit movement of the adjustable arm 517 and/or require greater actuation forces and/or more deliberate user control to manipulate the adjustable arm 517.

The illustrated adjustment mechanism may also be utilized to move the adjustable arm from the extended position shown in FIG. 15C to the retracted position of FIG. 15A by reversing the previously described procedure. From the extended position shown in FIG. 15C, the lever 550 is pulled back medially. This action pulls the lever arm 554, causing the pivot joint 552 to rotate about the hinge 542, which causes the coupled adjustable arm 517 to rotate to the transition position shown in FIG. 15B. From the transition position in FIG. 15B, the lever 550 may be moved back down, pressing the lever arm 554 forward laterally. The forward lateral movement of the lever arm 554 enables the pivot joint to continue rotating around the hinge 542, which causes the adjustable arm 517 to continue to rotate inward to the retracted position of FIG. 15A.

The illustrated adjustment mechanism enables adjustment from the retracted position to the extended position, and adjustment from the extended position to the retracted position, using the same lever actuation. For example, when the lever 550 is pulled medially to move the adjustable arm 517 from the retracted position of FIG. 15A to the transition position of FIG. 15B, subsequent return movement of the lever 550 typically happens quickly thereafter, while the adjustable arm 517 still has some rotational inertia. This ensures that the subsequent return movement of the lever 550 corresponds with the pivot joint 552 continuing its rotational path so as to further move the adjustable arm to the extended position, rather than stopping and reversing direction to return the adjustable arm to the retracted position. Likewise, when moving from the extended position to the retracted position, the lever 550 is typically pulled back and then returned in fast enough succession to ensure that the pivot joint 552 continues to rotate to the retracted position, rather than fighting against the momentum of the adjustable arm 517 to push it back to the extended position.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to a repair device of FIGS. 8 to 15C may be combinable with any element described in relation to a repair device of FIGS. 1A-7B.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An interventional system for repairing a heart valve, the interventional system comprising:
- a delivery device having a shaft; and
- an implantable repair device releasably attached to the shaft of the delivery device and defining a longitudinal axis, the implantable repair device comprising:
  - a first grasper extending outwardly relative to the longitudinal axis and having a first proximal gripping element and a first distal gripping element, the first proximal and distal gripping elements each having a medial end and a lateral end, wherein the first proximal gripping element is configured to contact an atrial side of a first leaflet of the heart valve and the first distal gripping element is configured to contact a ventricular side of the first leaflet such that the first proximal and distal gripping elements cooperate to grasp the first leaflet therebetween, wherein the first proximal and distal gripping elements collectively define a grasping length of the first grasper and along which the first proximal and distal gripping elements engage the first leaflet of the heart valve, and wherein the lateral end of each of the first proximal and distal gripping elements is moveable between a first position and a second position such that the grasping length of the first grasper is greater when the lateral ends of the first proximal and distal gripping elements are in the second position than in the first position, and wherein the medial end of each of the first proximal and distal gripping elements remains in a fixed position relative to the longitudinal axis when the lateral end moves between the first position and the second position, and
  - a second grasper extending outwardly relative to the longitudinal axis and having a second proximal gripping element and a second distal gripping element, the second proximal and distal gripping elements each having a medial end and a lateral end, wherein the second proximal gripping element is configured to contact an atrial side of a second leaflet of the heart valve and the second distal gripping element is configured to contact a ventricular side of the second leaflet such that the second proximal and distal gripping elements cooperate to grasp the second leaflet therebetween, wherein the second proximal and distal gripping elements collectively define a grasping length of the second grasper and along which the second proximal and distal gripping elements engage the second leaflet of the heart valve.

2. The system of claim 1, further comprising:
- a first control line extending from the delivery device and being operatively coupled to the first proximal gripping element for selectively moving the lateral end of the first proximal gripping element between the first and second position thereof, and
- a second control line extending from the delivery device and being operatively coupled to the first distal gripping element for selectively moving the lateral end of the first distal gripping element between the first and second position thereof.

3. The system of claim 2, wherein the first proximal and distal gripping elements are biased toward their respective second positions, and the first and second control lines are configured to move the first proximal and distal gripping elements to the second position upon releasing tension thereof.

4. The system of claim 1, wherein:
- the first proximal gripping element includes a first proximal arm and a second proximal arm, the first proximal arm defining the medial end of the first proximal gripping element, and the second proximal arm defining the lateral end of the first proximal gripping element and being moveable relative to the first proximal arm, and
- the first distal gripping element includes a first distal arm and a second distal arm, the first distal arm defining the medial end of the first distal gripping element, and the second distal arm defining the lateral end of the first distal gripping element and being moveable relative to the first distal arm.

5. The system of claim 4, wherein the first proximal arm includes a first group of frictional elements, the second proximal arm includes a second group of frictional elements, and moving the second proximal arm relative to the first proximal arm moves the second group of frictional elements relative to the first group of frictional elements.

6. The system of claim 4, wherein the first proximal arm includes a gear, the second proximal arm includes a plurality of teeth engaging the gear, and rotating the gear in first and second directions moves the second proximal arm between the respective first and second positions.

7. The system of claim 4, wherein the first proximal gripping element further includes a hinge, a lever, and a control line, the second proximal arm is coupled to the first proximal arm via the hinge, the lever is coupled to the hinge and the control line, and the control line extends from the delivery device such that tensioning the control line pivots the second proximal arm relative to the first proximal arm.

8. The system of claim 4, wherein the second proximal arm is slidably connected to the first proximal arm, and the second distal arm is slidably connected to the first distal arm.

9. The system of claim 4, wherein the second proximal arm is pivotably connected to the first proximal arm, and the second distal arm is pivotably connected to the first distal arm.

10. The system of claim 9, wherein the second proximal arm is pivotable relative to the first proximal arm in a clockwise direction, and the second distal arm is pivotable relative to the first distal arm in a counterclockwise direction.

11. An interventional system for repairing a heart valve, the interventional system comprising:

- a delivery device having a shaft; and
- an implantable repair device releasably attached to the shaft of the delivery device, the implantable repair device comprising:
  - a first grasper having a first proximal gripping element and a first distal gripping element, the first proximal and distal gripping elements being positionable on opposite sides of a first leaflet of the heart valve and being moveable relative to each other to grasp the first leaflet therebetween, wherein the first proximal and distal gripping elements collectively define a first grasping interface along which the first leaflet of the heart valve is engaged by the first proximal and distal gripping elements, and wherein the first proximal and distal gripping elements each have an adjustable length such that correspondingly adjusting the lengths of the first proximal and distal elements adjusts a length of the first grasping interface, and wherein a medial end of each of the first proximal and distal gripping elements defines a respective pivot axis about which a lateral end thereof is pivotable, and
  - a second grasper having a second proximal gripping element and a second distal gripping element, the second proximal and distal gripping elements being positionable on opposite sides of a second leaflet of the heart valve and being moveable relative to each other to grasp the second leaflet therebetween, wherein the second proximal and distal gripping elements collectively define a second grasping interface along which the second leaflet of the heart valve is engaged by the second proximal and distal gripping elements.

12. The system of claim 11, wherein the first proximal gripping element includes a plurality of frictional elements, the frictional elements at least partially defining the first grasping interface.

13. The system of claim 12, wherein the first proximal gripping element includes a first proximal arm defining the medial end of the first proximal gripping element and a second proximal arm defining the lateral end of the first proximal gripping element, the second proximal arm being moveable relative to the first proximal arm and including at least some of the frictional elements.

14. The system of claim 11, wherein the implantable repair device further includes a central portion defining a longitudinal axis thereof, the delivery device being releasably attached to the central portion.

15. The system of claim 14, wherein the first proximal and distal gripping elements extend from the central portion such that medial ends thereof are positioned closer to the longitudinal axis of the implantable repair device than lateral ends thereof, the medial ends being in a fixed position relative to the longitudinal axis.

16. An interventional system for repairing a heart valve, the interventional system comprising:

- a delivery device having a shaft; and
- an implantable repair device releasably attached to the shaft of the delivery device, the implantable repair device comprising:
  - a central portion defining a longitudinal axis of the implantable repair device,
  - a first grasper having a first proximal gripping element and a first distal gripping element, the first proximal and distal gripping elements being configured to cooperate with each other to grasp a first leaflet of the heart valve therebetween and each having a medial end, a lateral end, and an engagement area disposed between the medial end and the lateral end thereof for engagement against the first leaflet, wherein the engagement area of the first proximal gripping element is configured for engagement against a first side of the first leaflet and the engagement area of the first distal gripping element is configured for engagement against a second side of the first leaflet opposite the first side, wherein the lateral end of each of the first proximal and distal gripping elements is outwardly extendable relative to the medial end between a retracted position and an extended position such that the engagement area is greater when the lateral end is in the extended position than when the lateral end is in the retracted position, and wherein the medial end of each of the first proximal and distal gripping elements remains stationary relative to the longitudinal axis during extension and retraction of the lateral end, and
  - a second grasper having a second proximal gripping element and a second distal gripping element, the second proximal and distal gripping elements being configured to cooperate with each other to grasp a second leaflet of the heart valve therebetween and each having a medial end, a lateral end, and an engagement area disposed between the medial end and the lateral end thereof for engagement against the second leaflet, wherein the engagement area of the second proximal gripping element is configured for engagement against a first side of the second leaflet and the engagement area of the second distal gripping element is configured for engagement against a second side of the second leaflet opposite the first side.

17. The system of claim 16, wherein:

- the first proximal gripping element includes a first proximal arm defining the medial end of the first proximal gripping element and a second proximal arm defining the lateral end of the first proximal gripping element and being moveable relative to the first proximal arm, and
- the first distal gripping element includes a first distal arm defining the medial end of the first distal gripping element and a second distal arm defining the lateral end of the first distal gripping element and being moveable relative to the first distal arm.

18. The system of claim 17, further comprising:

a first control line coupled to the second proximal arm, extending medially from the second proximal arm toward the longitudinal axis of the implantable repair device, and extending proximally from the central portion and through the shaft of the delivery device so that tension applied to the first control line moves medially to correspondingly move the second proximal arm in a medial direction, and a second control line coupled to the second distal arm, extending medially from the second distal arm toward the longitudinal axis of the implantable repair device, and extending proximally from the central portion and through the shaft of the delivery device so that tension applied to the second control line moves medially to correspondingly move the second distal arm in a medial direction.

* * * * *